United States Patent
Garland et al.

(10) Patent No.: US 12,194,043 B2
(45) Date of Patent: Jan. 14, 2025

(54) URIDINE PHOSPHORYLASE INHIBITORS TO TREAT OR PREVENT PULMONARY DISEASE

(71) Applicant: Tosk, Inc., Mountain View, CA (US)

(72) Inventors: William A. Garland, Mountain View, CA (US); Philip Liaw, Mountain View, CA (US); Brian D. Frenzel, Mountain View, CA (US)

(73) Assignee: Tosk, Inc., Mountain View, CA (US)

(*) Notice: Subject to any disclaimer, the term of this patent is extended or adjusted under 35 U.S.C. 154(b) by 0 days.

(21) Appl. No.: 17/369,203

(22) Filed: Jul. 7, 2021

(65) Prior Publication Data

US 2022/0008422 A1    Jan. 13, 2022

Related U.S. Application Data

(60) Provisional application No. 63/048,850, filed on Jul. 7, 2020.

(51) Int. Cl.
*A61K 31/519* (2006.01)
*A61K 31/7072* (2006.01)
*A61P 11/00* (2006.01)

(52) U.S. Cl.
CPC ........ *A61K 31/519* (2013.01); *A61K 31/7072* (2013.01); *A61P 11/00* (2018.01)

(58) Field of Classification Search
None
See application file for complete search history.

(56) References Cited

U.S. PATENT DOCUMENTS

| | | |
|---|---|---|
| 5,296,216 A | 3/1994 | Turner |
| 5,470,838 A | 11/1995 | von Borstel et al. |
| 5,736,531 A | 4/1998 | von Borstel et al. |
| 5,968,914 A | 10/1999 | von Borstel et al. |
| 6,090,932 A | 7/2000 | McGee et al. |
| 6,232,298 B1 | 5/2001 | von Borstel et al. |
| 6,344,447 B2 | 2/2002 | von Borstel et al. |
| 6,992,072 B2 | 1/2006 | Walker |
| 7,166,581 B1 | 1/2007 | von Borstel et al. |
| 7,709,459 B2 | 5/2010 | von Borstel et al. |
| 7,776,838 B1 | 8/2010 | von Borstel et al. |
| 7,998,967 B2 | 8/2011 | Garland et al. |
| 8,853,227 B2 | 10/2014 | Garland et al. |
| 9,382,287 B2 | 7/2016 | Garland et al. |
| 9,700,547 B2 | 7/2017 | Basso et al. |
| RE48,253 E | 10/2020 | Garland et al. |
| 2004/0029823 A1 | 2/2004 | McKay et al. |
| 2004/0220134 A1 | 11/2004 | von Borstel et al. |
| 2005/0090551 A1 | 4/2005 | Campbell |
| 2006/0040890 A1 | 2/2006 | Martin et al. |
| 2008/0269185 A1 | 10/2008 | Rothstein et al. |
| 2009/0325969 A1 | 12/2009 | Garland et al. |
| 2011/0319419 A1 | 12/2011 | Garland et al. |
| 2012/0029071 A1 | 2/2012 | Biswal et al. |
| 2012/0189629 A1 | 7/2012 | Smith |
| 2012/0294869 A1* | 11/2012 | Pizzorno ................. A23L 33/10 514/44 R |
| 2014/0323427 A1 | 10/2014 | Idzko et al. |
| 2015/0072945 A1 | 3/2015 | Garland et al. |
| 2016/0193354 A1 | 7/2016 | Noe et al. |
| 2020/0397790 A1 | 12/2020 | Garland et al. |
| 2021/0236530 A1 | 8/2021 | Garland et al. |
| 2022/0008422 A1 | 1/2022 | Garland et al. |

FOREIGN PATENT DOCUMENTS

| | | | |
|---|---|---|---|
| EP | 0801062 A1 | 10/1997 | |
| JP | H06508846 A | 10/1994 | |
| JP | H10511689 A | 11/1998 | |
| KR | 101195019 B1 | 10/2012 | |
| WO | WO9301202 A1 | 1/1993 | |
| WO | WO9426761 A1 | 11/1994 | |
| WO | WO-9601115 A1 * | 1/1996 | ............. A61K 31/00 |
| WO | WO03099297 A1 | 12/2003 | |
| WO | WO2004024095 A2 | 3/2004 | |
| WO | WO-2005020885 A2 * | 3/2005 | ......... A61K 31/7052 |
| WO | WO2005026186 A1 | 3/2005 | |
| WO | WO2008083465 A1 | 7/2008 | |
| WO | WO2009114325 A2 | 9/2009 | |
| WO | WO2020036974 A1 | 2/2020 | |
| WO | WO2020036975 A1 | 2/2020 | |
| WO | WO2020036982 A1 | 2/2020 | |

OTHER PUBLICATIONS

Golovinski et al. "Antiviral, Antibacterial and Antitumor Activity of the Hydrazide and the Ethyl Ester of 2,2'-Anhydro-I-(p-D-arabinofuranosyl)-orotic Acid," Arzneim.-Forsch. Drug Res. 30 (II), Nr. 12 (1980). (Year: 1980).*
Cicko et al. "Uridine supplementation exerts anti-inflammatory and anti-fibrotic effects in an animal model of pulmonary fibrosis," Cicko et al. Respiratory Research (2015) 16:105. (Year: 2015).*
Da Silva et al., Therapeutic effect of uridine phosphorylase 1 (UPP1) inhibitor on liver fibrosis in vitro and in vivo, European Journal of Pharmacology, Jan. 2021, vol. 890, No. 173670, p. 1-11.
Leyva et al., Phase I and Pharmacokinetic Studies of High-Dose Uridine Intended for Rescue from 5-Fluorouracil Toxicity, Cancer Research, Dec. 1984, vol. 44, p. 5928-5933.

(Continued)

*Primary Examiner* — Jeffrey S Lundgren
*Assistant Examiner* — Michael J Schmitt
(74) *Attorney, Agent, or Firm* — Darya C. Cheng; Bret E. Field; Bozicevic, Field & Francis LLP

(57) ABSTRACT

The present invention relates to compositions, formulations, and methods for treating pulmonary disorders having fibrosis as part of the underlying pathology, such as IPF and ARDS, by administration of a UPase inhibitor, with or without supplemental UR, a UR prodrug, or a UR mimetic to a subject in need thereof.

20 Claims, 7 Drawing Sheets

(56) References Cited

OTHER PUBLICATIONS

Maria et al., Radiation-Induced Oral Mucositis, Frontiers in Oncology, May 2017, vol. 7, Art. 89, p. 1-23.

Renck et al., Human uridine phosphorylase-1 inhibitors: a new approach to ameliorate 5-fluorouracil-induced Intestinal mucositis, Invest New Drugs, Jul. 2014, vol. 32, p. 1301-1307.

Al Safarjalani et al., 5-(Phenylthio)acyclouridine: a powerful enhancer of oral uridine bioavailability: relevance to chemotherapy with 5-fluorouracil and other uridine rescue regiments, Cancer Chemother Pharmacol, Feb. 2005, vol. 55, p. 541-551.

Le et al., Uridine Prevents Fenofibrate-Induced Fatty Liver, PLoS One, Jan. 2014, vol. 9, No. 1, p. 1-14.

Cicko et al., Uridine supplementation exerts anti-inflammatory and anti-fibrotic effects in an animal model of pulmonary fibrosis, Respiratory Research, 2015, vol. 16, No. 105, p. 1-10.

Labbe et al., Drug-induced liver injury through mitochondrial dysfunction: mechanisms and detection during preclinical safety studies, Fundamental & Clinical Pharmacology, Aug. 2008, vol. 22, No. 4, p. 335-353.

Goncalves da Silva et al., Therapeutic effect of uridine phosphorylase 1 (UPP1) inhibitor on liver fibrosis in vitro and in vivo, European Journal of Pharmacology, 2021, vol. 890, No. 173670, p. 1-11.

Ashour et al., 5-(m-Benzyloxybenzyl)barbituric acid acyclonucleoside, a uridine phosphorylase inhibitor, and 2',3',5'-tri-O-acetyluridine, a prodrug of uridine, as modulators of plasma uridine concentration. Implications for chemotherapy, Biochem Pharmacol (1996), 51(12):1601-1611.

Ashour et al., Effect of 5-(phenylselenenyl)acyclouridine, an inhibitor of uridine phosphorylase, on plasma concentration of uridine released from 2',3',5'-tri-O-acetyluridine, a prodrug of uridine: relevance to uridine rescue in chemotherapy, Cancer Chemother Pharmacol (2000), 46(3):235-240.

Ashour et al., Modulation of 5-fluorouracil host toxicity by 5-(benzyloxybenzyl)barbituric acid acyclonucleoside, a uridine phosphorylase inhibitor, and 2',3',5'-tri-O-acetyluridine, a prodrug of uridine, Biochem Pharmacol (2000), 60(3):427-431.

Brunetti et al., 5-Fluorouracil enhances azidothymidine cytotoxicity: in vitro, in vivo, and biochemical studies, Cancer Res (1990), 50(13):4026-4031.

Christensen et al., Effect of hydration on methotrexate plasma concentrations in children with acute lymphocytic leukemia, J Clin Oncology (1988), 6(5):797-801.

Darnowski et al., Fluorouracil plus azidothymidine cytotoxicity in vitro: Relationship to cellular thymidine kinase activity, Proc of American Assoc for Cancer Research (1990), 31:398.

Darnowski et al., Resistance to Azido-Thymidine Cytotoxicity in the Human Colon Tumor Cell Line HCT15 is Associated with Enhanced Removal of AZT from Cellular DNA, Proc of American Assoc for Cancer Research (1991), 32:358.

Drabikowska et al., Inhibitor properties of some 5-substituted uracil acyclonucleosides, and 2,2'-anhydrouridines versus uridine phosphorylase from *E. coli* and mammalian sources, Biochem Pharmacol (1987), 36(23):4125-4128.

Ettmayer et al., Lessons learned from marketed and investigational prodrugs, Medicinal Chemistry (2004), 47(10):2393-2404.

Howell et al., Cytokinetic comparison of thymidine and leucovorin rescue of marrow in humans after exposure to high-dose methotrexate, Cancer Res (1979), 39(4):1315-1320.

Howell et al., Thymidine Rescue of High-Dose Methotrexate in Humans, Cancer Res (1978), 38(2): 325-330.

Iigo et al., Differential effects of 2,2'-anhydro-5-ethyluridine, a uridine phosphorylase inhibitor, on the antitumor activity of 5-fluorouridine and 5-fluoro-2'-deoxyuridine, Biochem Pharmacol (1990), 39(7):1247-1253.

Martin et al., High-dose 5-fluorouracil with delayed uridine "rescue" in mice, Cancer Res (1982), 42(10):3964-3970.

Martin et al., Use of oral uridine as a substitute for parenteral uridine rescue of 5-fluorouracil therapy, with and without the uridine phosphorylase inhibitor 5-benzylacyclouridine, Cancer Chemother Pharmacol (1989), 24(1):9-14.

Mazokopakis et al., Wild chamomile (*Matricaria recutita* L.) mouthwashes in methotrexate-induced oral mucositis, Phytomedicine (2005), 12(1-2):25-27.

Morissette et al., High-throughput crystallization: polymorphs, salts, co-crystals and solvates of phramaceutical solids, Adv Drug Deliv Rev (2004), 56(3):275-300.

Newman et al., Increased Sensitivity to Azidothymidine in a Subline of CCRF-CEM Human Leukemia Cells Resistant to Methotrexate, Proceedings of the American Assoc. for Cancer Research (1991), 32:413.

Pizzorno et al., Phase I clinical and pharmacological studies of benzylacyclouridine, a uridine phosphorylase inhibitor, Clin Cancer Res (1998), 4(5):1165-1175.

Scanlon et al., Overexpression of DNA replication and repair enzymes in cisplatin-resistant human colon carcinoma HCT8 cells and circumvention by azidothymidine, Cancer Commun (1989), 1(4):269-275.

Semon et al., Potentiation of the Antitumor Activity of Methotrexate by Concurrent Infusion of Thymidine, Cancer Res (1978), 38:2905-2911.

Stella, Prodrugs as therapeutics, Expert Opinion on Therapeutic Patents (2004), 14,(3):277-280.

Sterba et al., High-dose methotrexate and/or leucovorin rescue for the treatment of children with lymphoblastic malignancies: do we really know why, when and how?, Neoplasma (2005), 52 6):456-463.

Tattersall et al., The reversal of methotrexate toxicity by thymidine with maintenance of antitumour effects, Nature (1975), 253 (5488):198-200.

Testa, Prodrug research: futile or fertile?, Biochemical Pharmacology (2004), 68(11):2097-2106.

Tosi et al., Azidothymidine-induced cytotoxicity and incorporation into DNA in the human colon tumor cell line HCT-8 is enhanced by methotrexate in vitro and in vivo, Cancer Res (1992), 52(15):4069-4073.

Veres et al., 5-Substituted-2,2'-anhydrouridines, potent inhibitors of uridine phosphorylase, Biochem Pharmacol (1985), 34(10):1737-1740.

Veres et al., Inhibition of uridine phosphorylase by pyrimidine nucleoside analogs and consideration of substrate binding to the enzyme based on solution conformation as seen by NMR spectroscopy, Eur J Biochem (1988), 178(1):173-181.

Vippagunta et al. Crystalline solids, Adv Drug Deliv Rev (2001), 48(1):3-26.

Weber et al., Azidothymidine inhibition of thymidine kinase and synergistic cytotoxicity with methotrexate and 5-fluorouracil in rat hepatoma and human colon cancer cells, Cancer Commun (1990), 2(4):129-133.

Weber et al., AZT: a biochemical response modifier of methotrexate and 5-fluorouracil cytotoxicity in human ovarian and pancreatic carcinoma cells, Cancer Commun (1991), 3(4):127-132.

Weber et al., Regulation of de novo and salvage pathways in chemotherapy, Adv Enzyme Regul (1991), 31:45-67.

Wolff, Burger's Medicinal Chemistry and Drug Discovery, 5th edition (1994), vol. 1, pp. 975-977.

Veres et al., "The effect of the 3'-OH group on the conformation and binding ability of anhydropyrimidine nucleosides to uridine phosphorylase", Archives of Biochemistry and Biophysics, Apr. 1991, vol. 286, No. 1, pp. 1-5, abstract only.

Grancharov et al., "Inhibition of uridine phosphorylase by some pyrimidine derivatives", Biochemical Pharmacology, 1991, vol. 41, p. 1769-1772, abstract only.

Iigo et al., "In vivo Antitumor Effects of Fluoropyrimidines on Colon Adenocarcinoma 38 and Enhancement by Leucovorin", Jpn. J. Cancer Res., 1992, vol. 83, p. 392-396.

Karimi Khezri et al., Anti-Apoptotic and Anti-Oxidant Effects of Systemic Uridine Treatment in an Experimental Model of Sciatic Nerve Injury, Turk Neurosurg, Mar. 2021, p. 1-6.

(56) References Cited

OTHER PUBLICATIONS

Sonis, Superoxide Dismutase as an Intervention for Radiation Therapy-Associated Toxicities: Review and Profile of Avasopasem Manganese as a Treatment Option for Radiation-Induced Mucositis, Drug Design, Development and Therapy, Mar. 2021, vol. 15, p. 1021-1029.

Xiang et al., Protective effect of Andrographolide on 5-Fu induced intestinal mucositis by regulating p38 MAPK signaling pathway, Life Sciences, Jul. 2020, vol. 252, 117612, p. 1-12.

Lee et al., Dipeptidyl-peptidase-4 (DPP-4) inhibitor ameliorates 5-flurouracil induced intestinal mucositis, BMC Cancer, Oct. 2019, vol. 19, No. 1016, p. 1-9.

Mironova et al., Prospects for the use of regulators of oxidative stress in the comprehensive treatment of the novel Coronavirus Disease 2019 (COVID-19) and its complications, European Review for Medical and Pharmacological Sciences, 2020, vol. 24, p. 8585-8591.

Mosentsov et al., Does the Operation of Mitochondrial ATP-Dependent Potassium Channels Affect the Structural Component of Mitochondrial and Endothelial Dysfunctions in Experimental Parkinsonism?, Bulletin of Experimental Biology and Medicine, Feb. 2021, vol. 170, No. 4, p. 431-435.

PubChem CID 73805817, May 29, 2014, Retrieved from the Internet on May 4, 2022, URL: https://pubchem.ncbi.nlm.nih.gov/compound/73805817, 8 pages.

Tang et al., Inhibition of Autotaxin with GLPG1690 Increases the Efficacy of Radiotherapy and Chemotherapy in a Mouse Model of Breast Cancer, Molecular Cancer Therapeutics, Sep. 23, 2019, p. 1-13.

Saif et al., 5-Fluorouracil dose escalation enabled with PN401 (triacetyluridine): toxicity reduction and increased antitumor activity in mice, Cancer Chemother Pharmacol, 2006, vol. 58, p. 136-142.

Sonis et al., Phase II investigational oral drugs for the treatment of radio/chemotherapy induced oral mucositis, Expert Opinion on Investigational Drugs, Jan. 2018, vol. 27, No. 2, p. 147-154.

Yuan et al., Emerging therapies for the prevention and treatment of oral mucositis, Expert Opinion on Emerging Drugs, Aug. 2014, vol. 19, No. 3, p. 343-351.

Zidan et al., Multidrug Chemotherapy Using Bleomycin, Methotrexate, and Cisplatin Combined with Radical Radiotherapy in Advanced Head and Neck Cancer, Cancer, Jan. 1987, vol. 59, No. 1, p. 24-26.

Connolly et al., Uridine and its nucleotides: biological actions, therapeutic potentials, Trends Pharmacol Sci, May 1999, vol. 20, No. 5, p. 218-225.

Melichar et al., Intestinal permeability in patients with chemotherapy-induced stomatitis, J Cancer Res Clin Oncol, May 2001, vol. 127, No. 5, p. 314-318.

Shannahoff et al., 2,2'-Anhydropyrimidine nucleosides. Novel syntheses and reactions, J. Org. Chem., Feb. 1973, vol. 38, No. 3, p. 593-598.

Gupta et al., A randomised clinical trial to contrast radiotherapy with radiotherapy and methotrexate given synchronously in head and neck cancer, Clinical Radiology, 1987, vol. 38, p. 575-581.

Roberts et al., Selective prebiotic conversion of pyrimidine and purine anhydronucleosides into Watson-Crick base-pairing arabinofuranosyl nucleosides in water, Nature Communications, 2018, vol. 9, No. 4073, p. 1-10.

Seiter et al., Uridine allows dose escalation of 5-fluorouracil when given with N-phosphonacetyl-L-aspartate, methotrexate, and leucovorin, Cancer, Mar. 1993, vol. 71, No. 5, p. 1875-1881.

Mundt et al., Pulmonary fibrosis after chemotherapy with oxaliplatin and 5-fluorouracil for colorectal cancer, Oncology, 2007, vol. 73, Nos. 3-4, Abstract only, 2 pages.

* cited by examiner

FIG. 3A: Group 1 - Naïve - Animal 34 299. Section of the lungs stained by Masson's trichrome No abnormality detected (Grade 0).

FIG. 3B: Group 2 - Vehicle - Animal 38 303. Section of the lungs stained by Masson's trichrome.
Green arrows indicate a focus of fibrosis Grade 3 increased fibrosis with definite damage to lung structure and formation of fibrous bands or small fibrous masses.
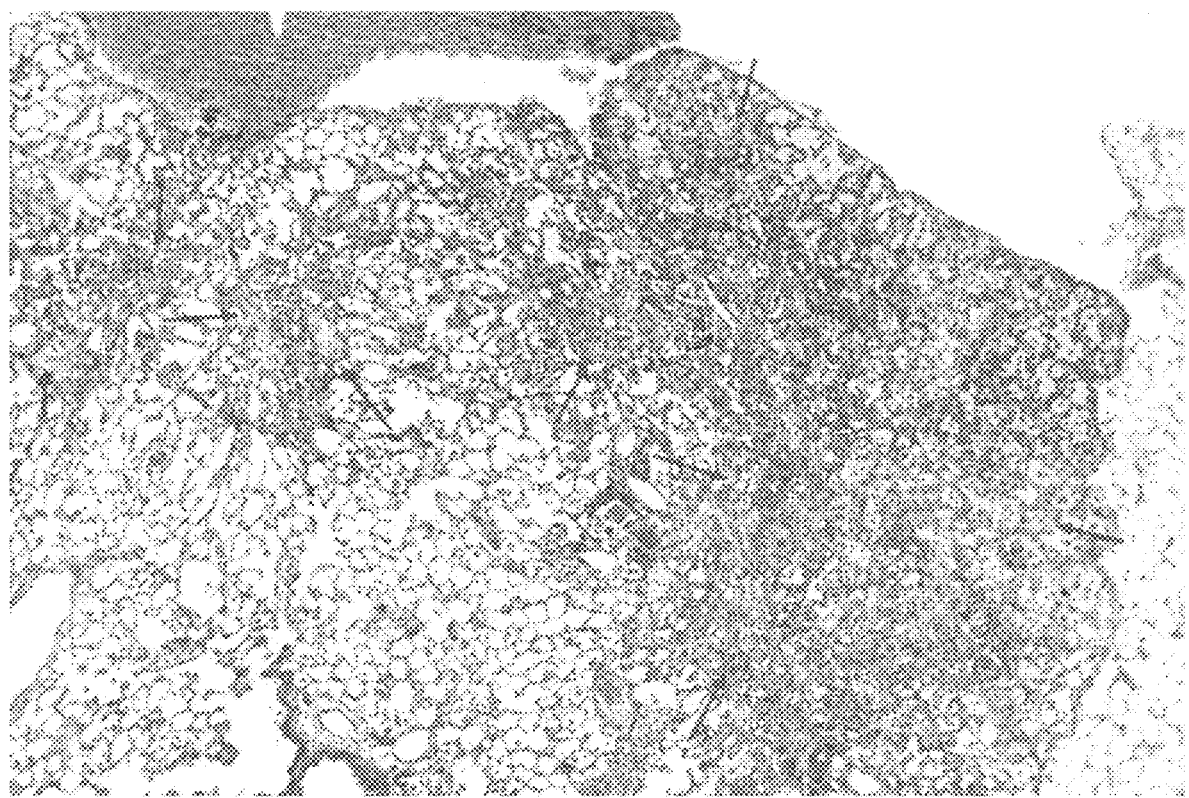

FIG. 3C: Group 3 - Uridine - Animal 47 312. Section of the lungs stained by Masson's trichrome.
Green arrows indicate a focus of fibrosis Grade 3 increased fibrosis with definite damage to lung structure and formation of fibrous bands or small fibrous masses.
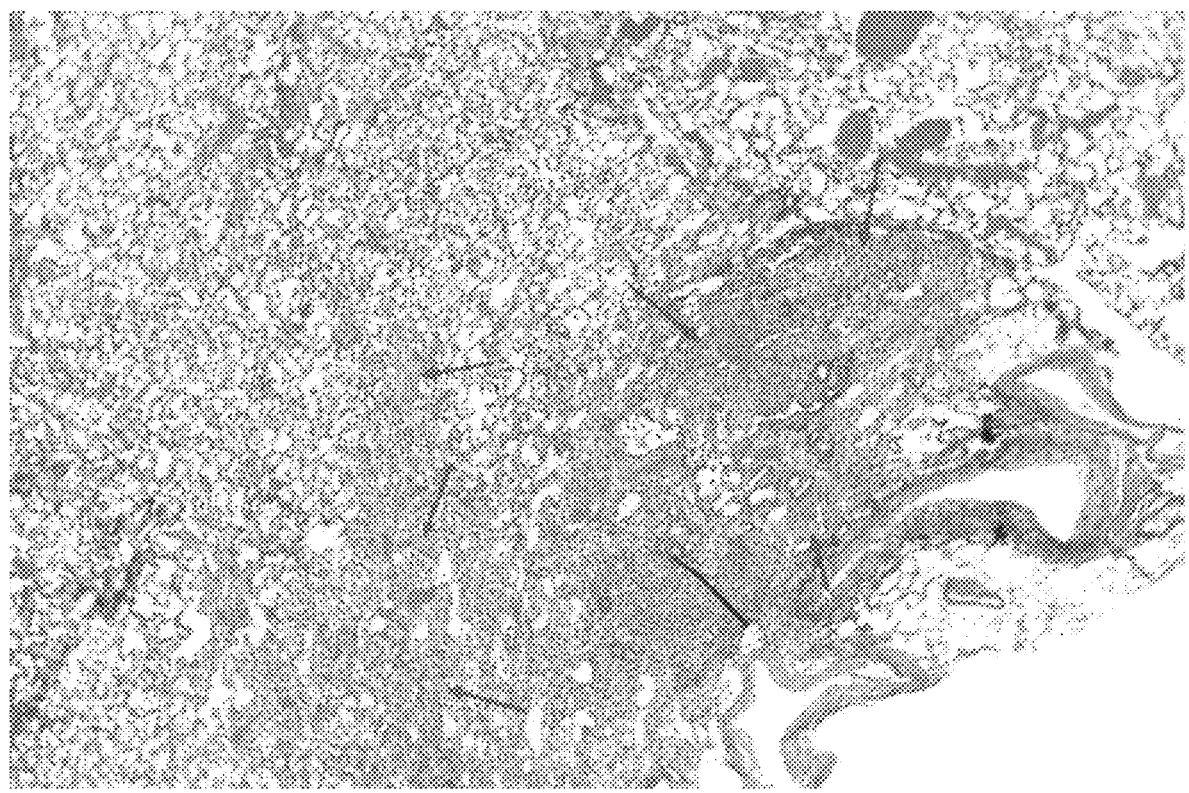

FIG. 3D: Group 4 – Test item 1 - Animal 59 324. Section of the lungs stained by Masson's trichrome.
Green arrows indicate a focus of fibrosis Grade 2 moderate thickening of walls without obvious damage to lung architecture.
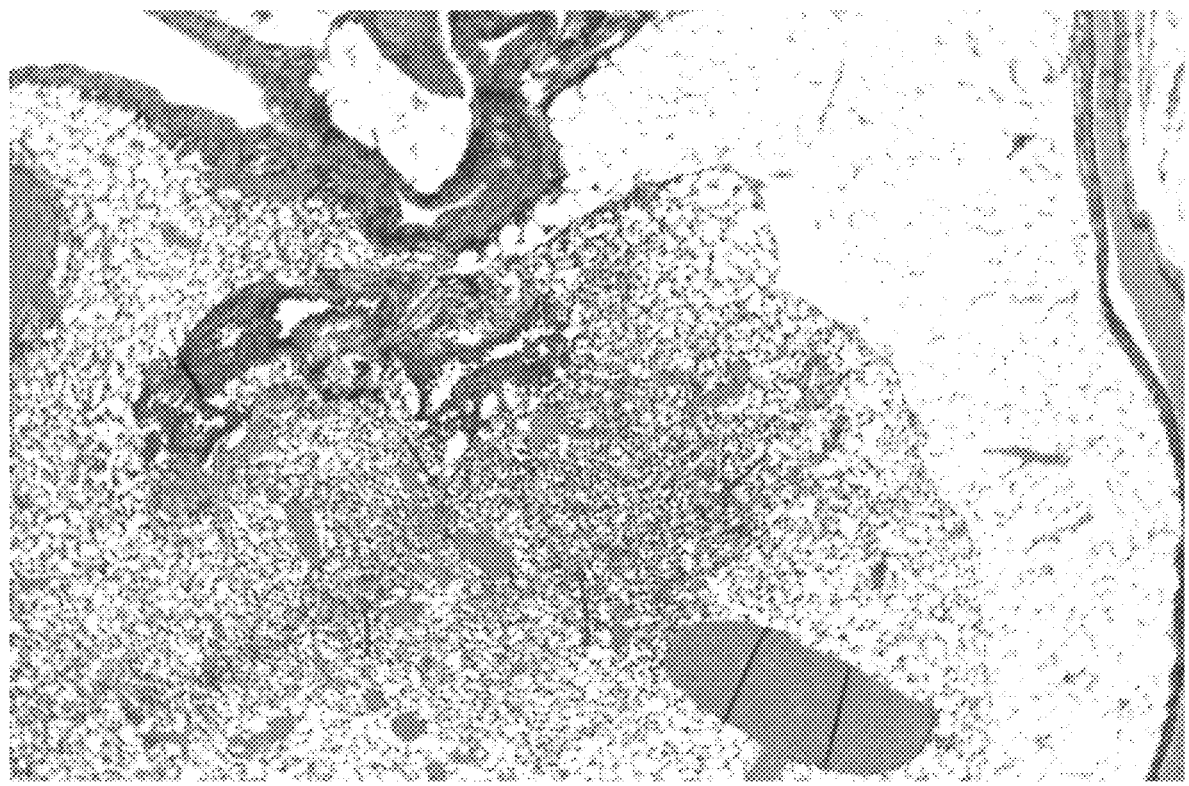

URIDINE PHOSPHORYLASE INHIBITORS TO TREAT OR PREVENT PULMONARY DISEASE

CROSS-REFERENCE TO RELATED APPLICATIONS

Pursuant to 35 U.S.C. § 119(e), this application claims priority to the filing date of U.S. Provisional Patent Application Ser. No. 63/048,850 filed Jul. 7, 2020; the disclosure of which application is herein incorporated by reference

INTRODUCTION

Fibrosis (Rockey D C, Bell P D, Hill J A, Fibrosis—A Common Pathway to Organ Injury and Failure, N Engl J Med 2015; 372:1138-1149) is pathological wound healing where connective tissue replaces normal parenchymal tissue leading to tissue re-modelling and the formation of permanent scar tissue (fibrotic scarring). Fibrosis is a sequela of impaired wound healing from repetitive, extensive, epithelial injury. Normal, healthy wound healing is a natural restorative process in which an organ repairs itself after injury. Impaired wound healing occurs when the wound healing process enters a state of pathologic inflammation and scar formation because of a postponed, incomplete, or uncoordinated healing process. Fibrosis is the final, common pathological outcome of many chronic inflammatory diseases affecting organ tissues. (Wynn T A, Ramalingam T R, Mechanisms of fibrosis: therapeutic translation for fibrotic disease, Nature Medicine 2012; 18:1028-1040).

Impaired wound healing followed by resulting pathologic fibrosis constitute a major health problem worldwide (fibrotic diseases; Rosenbloom J, Macarak E, Piera-Velazquez S, Jimenez S A, Human Fibrotic Diseases: Current Challenges in Fibrosis Research, Fibrosis, Part of the Methods in Molecular Biology book series, MIMB, Vol. 1627, pg. 1-23) because of:

The large number of affected individuals,
The limited knowledge of the pathogenesis of the fibrotic process,
The marked heterogeneity in fibrotic etiologies and clinical manifestations,
The absence of appropriate and fully validated biomarkers, and,
Most importantly, the lack of effective, preventative and disease-modifying therapeutic agents available to patients suffering from, or at risk for, fibrosis.

Fibrotic disorders encompass a wide spectrum of clinical entities including, systemic fibrotic diseases such as systemic sclerosis (SSc), sclerodermatous graft vs. host disease, and nephrogenic systemic fibrosis, and numerous organ-specific disorders including, radiation-induced fibrosis and cardiac, pulmonary, liver, and kidney fibrosis. The causative mechanisms of fibrotic disorders are diverse, and, in many cases, unknown. These diseases share the common feature of an uncontrolled and progressive accumulation of fibrotic tissue in affected organs causing their dysfunction and ultimate failure. Despite the remarkable heterogeneity in the etiologic mechanisms responsible for the development of fibrotic diseases and their clinical manifestations, numerous studies have identified activated myofibroblasts as a common cellular element ultimately responsible for the replacement of normal tissues with nonfunctional, fibrotic tissue. The therapeutic targets most investigated to mitigate pathologic fibrosis are those initiated by transforming growth factor-β (TGF-β). (Meng X M, Nikolic-Paterson D J, Lan H Y, TGF-β: the master regulator of fibrosis, Nature Reviews Nephrology 2016; 12:325-338). Other approaches studied include numerous cytokines and signaling molecules, which stimulate profibrotic reactions in myofibroblasts. (Weiskirchen R, Weiskirchen S, Tacke F, Organ and tissue fibrosis: Molecular signals, cellular mechanisms and translational implications, Molecular Aspects of Medicine 2019; 65:2-15).

Pulmonary fibrosis is a particularly injurious manifestation of impaired wound healing. Pulmonary conditions with fibrosis as part of the underlying pathophysiology are often collected under the term Interstitial Lung Diseases (ILDs). (du Bois R M, Strategies for treating idiopathic pulmonary fibrosis, Nature Reviews Drug Discovery 2010; 9:129-140). ILDs include a large and diverse group of more than 200 lung diseases and respiratory conditions characterized by inflammation and fibrosis of the interstitium, the tissue located between the air sacs of the lung.

Two of the most common types of ILD are idiopathic pulmonary fibrosis (IPF) and acute respiratory disease (ARDS). Other ILDs with similar pathological fibrotic alterations in the lung interstitium and a progressive fibrosis include, connective tissue disease-associated ILD (CTD-ILD), which is mainly systemic sclerosis-ILD (SSc-ILD), rheumatoid arthritis-ILD (RA-ILD), idiopathic non-specific interstitial pneumonia (i SIP), chronic hypersensitivity pneumonitis (CHP), unclassifiable idiopathic interstitial pneumonia (IIP), interstitial pneumonia with autoimmune features (IPAF), and environmental/occupational fibrosing lung diseases such as those caused by asbestosis and silica.

The most prominent ILDs are IPF and ARDS.

Idiopathic pulmonary fibrosis (IPF) is a chronic, progressive disease with high mortality that commonly occurs in middle-aged and older adults. (Glass D S, Grossfeld D, Renna H A, Agarwala P, Spiegler P, Kasselman L J, Glass A D, DeLeon J, Reiss A B, Idiopathic pulmonary fibrosis: Molecular mechanisms and potential treatment approaches, Respiratory Investigation 2020; 58(5): 320-335; Richeldi L, Collard H R, Jones M G, Idiopathic pulmonary fibrosis, Lancet. 2017 May 13; 389 (10082):1941-1952). IPF is characterized by progressive fibrosis of the interstitium of the lung, leading to decreasing lung volume as determined by forced vital capacity (FVC) and progressive pulmonary insufficiency.

The decline in lung function caused by IPF often manifests as exertional dyspnea and cough. Symptoms result from a fibrotic process driven by alveolar epithelial cells that leads to increased migration, proliferation, and differentiation of lung fibroblasts. Ultimately, the differentiation of fibroblasts into myofibroblasts, which synthesize excessive amounts of extracellular matrix proteins, destroys the lung architecture. However, the factors that induce the fibrotic process are unclear, and diagnosis can be difficult. Practical biomarkers to improve diagnostic and prognostic accuracy are lacking. High-resolution computed tomography typically shows interstitial pneumonia with basal and peripheral honeycombing. Gas exchange and diffusion capacity are impaired. Treatments are limited. Lung transplantation is often contraindicated because of age and comorbidities, but it improves survival when successful. Two drugs recently approved to treat IPF, pirfenidone (Gulati S, Luckhardt T R, Updated Evaluation of the Safety, Efficacy and Tolerability of Pirfenidone in the Treatment of Idiopathic Pulmonary Fibrosis, Drug Healthc Patient Saf. 2020 May 7; 12:85-94) and nintedanib, (Rodríguez-Portal J A, Efficacy and Safety of Nintedanib for the Treatment of Idiopathic Pulmonary Fibrosis: An Update, Drugs R D. 2018; 18: 19-25) only slow the progression of the disease. The incidence and prevalence of IPF has been increasing, and there is an urgent need for improved therapies. (Martinez F J, Collard H R, Pardo A, Raghu G, Richeldi L, Selman M, Swigris J J, Taniguchi H, Wells A U, Idiopathic pulmonary fibrosis, Nat Rev Dis Primers. 2017; 3: 17074).

Acute respiratory distress syndrome (ARDS) (Bos L D, Martin-Loeches I, Schultz M J, ARDS: challenges in patient care and frontiers in research, Eur Respir Rev. 2018; 27 (147):170107) is a condition that causes fluid to build up in a patient's lungs so oxygen cannot reach the patient's organs. Fluid leaks from small blood vessels and collects in tiny air sacs in lungs preventing the sacs from filling with air. ARDS can advance quickly and can be life-threatening. Causes of ARDS include, sepsis, accidents, breathing in harmful things such as dense smoke or chemical fumes, pneumonia, transfusion, inflamed pancreas, reactions to certain medications like amiodarone, (Papiris S A, Triantafillidou C, Kolilekas L, Markoulaki D, Manali E D, Amiodarone: review of pulmonary effects and toxicity, Drug Saf. 2010; 33(7): 539-58) drug overdose, near-drowning, burns, and aspiration of food. Symptoms include shortness of breath, low blood pressure, unusually fast breathing, fast heartbeat, cough, fever, chest pain, especially when breathing deeply, confusion and exhaustion, blue-tinted lips or nails from lack of arterial oxygen, and dizziness. There is no test to identify ARDS. Treatments include a breathing tube or a ventilator. Most treatment of ARDS is done in the ICU, where the overall hospital mortality rate is typically about 40%.

The pathophysiology of ARDS involves interactions among multiple mechanisms, including, immune cell infiltration, cytokine storm, alveolar-capillary barrier disruption, and cell apoptosis. These are followed by an organizing phase with alveolar septal fibrosis and vastly diminished lung function (Cardinal-Fernández P, Lorente J A, Ballén-Barragán A, Matute-Bello G, Acute Respiratory Distress Syndrome and Diffuse Alveolar Damage: New Insights on a Complex Relationship, Ann Am Thorac Soc. 2017; 14(6): 844-850).

COVID-19 and Lung Fibrosis. (George P M, Wells A U, Jenkins R G, Pulmonary fibrosis and COVID-19: the potential role for antifibrotic therapy, Lancet Respir Med. 2020 May 15: S2213-2600(20)30225-3; Spagnolo P, Balestro E, Aliberti S, Cocconcelli E, Biondine D, Cas G D, Sverzellati N, Maher, T M, Pulmonary fibrosis secondary to COVID-19: a call to arms?, Lancet Respir Med. 2020. 15; S2213-2600(20)30222-8). To date, millions of people worldwide been infected with Covid-19 and hundreds of thousands have died. Despite many efforts to develop vaccines and antiviral therapies for Covid-19, most virologists expect there will be no quick solution to this pandemic, and that Covid-19 will continue to be a serious, global health threat for the foreseeable future. Almost all COVID-19 patients with severe disease present with pneumonia featuring lung abnormalities including, lower lobe glass opacities with, or without, consolidation, noticeable on x-ray. Many patients are diagnosed with ARDS with associated pulmonary fibrosis. The mechanisms by which COVID-19 causes lung damage are not completely understood. The most plausible contributor is the cytokine release syndromeistorm triggered by the SARS Cov-2 antigen. Other proposed contributors include, drug-induced pulmonary toxicity, high airway pressure, and hyperoxia induced acute lung injury secondary to mechanical ventilation.

In addition to the immediate contribution of lung dysfunction to the lethality of COVID-19, long-term impairment of lung function, post infection, is a serious concern for the millions of individuals who survive COVID-19.

SUMMARY

Methods are provided for treating patients suffering from pulmonary disease having fibrosis as the pathologic endpoint, such as IPF, ARDS, virus induced fibrosis, etc., using a UPase inhibitor. Aspects of the methods include administering an effective amount of a UPase inhibitor, with or without supplemental UR, to the subject. In certain embodiments, the agent is a 2,2'-anhydropyrimidine, or a derivative thereof. Also provided are compositions for use in practicing the subject methods. The subject methods and compositions find use in a variety of different pulmonary conditions.

DEFINITIONS

Figure 1:
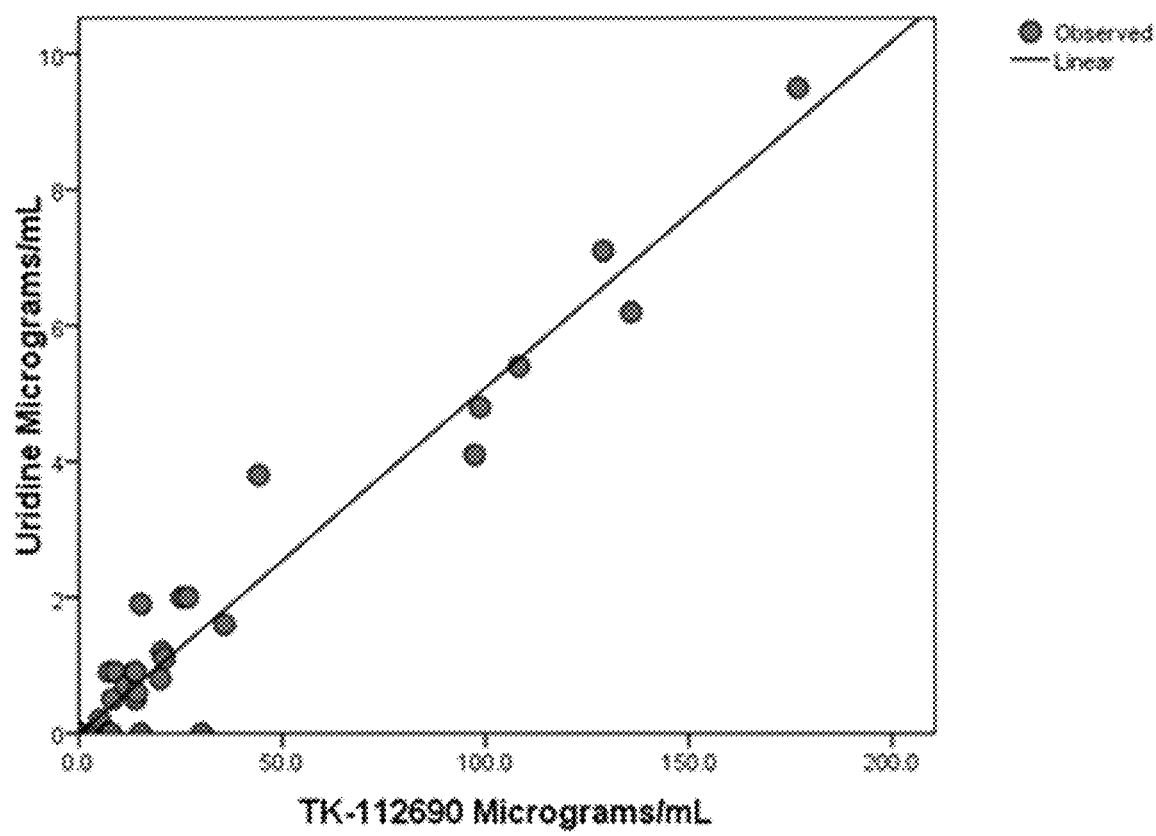
FIG. 1. Figure provides a regression analysis of plasma UR concentration versus plasma Compound 1 concentrations determined following continuous infusion of various amounts of TK-112690 to mice. R2 for the line is 0.95, and the slope and intercept values for the line are 0.010 and 0.051, respectively. TK-112690 is seen to elevate plasma UR in a linear fashion.

The following terms have the following meanings unless otherwise indicated when describing the compounds, pharmaceutical compositions containing such compounds, methods of using such compounds and compositions, and the description of the biology and pharmacology for use of the compounds, It should also be understood that any of the moieties defined forth below may be substituted with a variety of substituents, and that the respective definitions are intended to include such substituted moieties within their scope.

"Acyl" refers to a radical —C(O)R, where R is hydrogen, alkyl, cycloalkyl, heterocycloalkyl, aryl, arylalkyl, heteroalkyl, or heteroaryl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, heterocycloalkyl, aryl, arylalkyl, heteroalkyl, heteroaryl, heteroarylalkyl and R is hydrogen, alkyl, alkoxy, cycloalkyl, heterocycloalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)-cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkynyl and alkynylene. Aliphatic groups typically have from 1 or 2 to 6 or 12 carbon atoms.

"Alkenyl" refers to monovalent olefinically unsaturated hydrocarbyl aroups having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Alkoxycarbonylamino" refers to the group —NRC(O)OR' where R is hydrogen, alkyl, aryl or cycloalkyl, and R' is alkyl or cycloalkyl.

"Alkyl" refers to monovalent saturated aliphatic hydrocarbyl groups particularly having up to about 12 or 18 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, isobutyl, tert-butyl, n-hexyl, n-octyl, tert-octyl and the like. The term "alkyl" also includes "cycloalkyls" as defined herein.

Structures for a few exemplary alkyl groups are provided in Table 1 below.

TABLE 1

Structure of exemplary alkyl groups

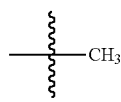

Methyl

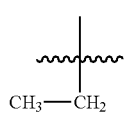

Ethyl

TABLE 1-continued

Structure of exemplary alkyl groups

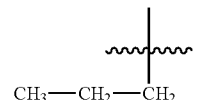

Propyl

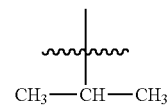

Isopropyl

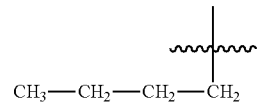

Butyl

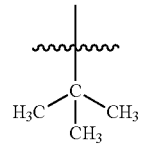

tert-Butyl

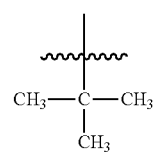

sec-Butyl

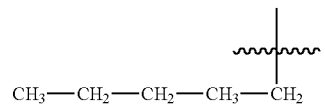

Pentyl

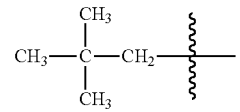

Neopentyl

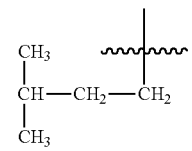

Isopentyl

Hexyl

TABLE 1-continued

Structure of exemplary alkyl groups

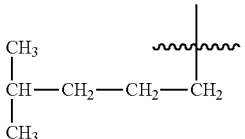

Isohexyl

"Alkylene" refers to divalent saturated aliphatic hydrocarbyl groups particularly having up to about 12 or 18 carbon atoms and more particularly 1 to 6 carbon atoms which can be straight-chained or branched, This term is exemplified by groups such as methylene (—CH$_2$—), ethylene (—CH$_2$CH$_2$—), the propylene isomers (eg, —CH$_2$CH$_2$CH$_2$— and —CH(CH$_3$)CH$_2$—) and the like.

"Alkynyl" refers to acetylenically unsaturated hydrocarbyl groups particularly having up to about 12 or 18 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Amino" refers to the radical —NH$_2$.

"Amino acid" refers to any of the naturally occurring amino acids (eg Ala, Arg, Asn, Asp, Cys, Glu, Gln, Gly, His, Hyl, Hyp, He, Leu, Lys, Met, Phe, Pro, Ser, Thr, Trp, Tyr, and Val) in D, L, or DL form. The side chains of naturally occurring amino acids are well known in the art and include, for example, hydrogen (eg, as in glycine), alkyl (eg, as in alanine, valine, leucine, isoleucine, proline), substituted alkyl (eg, as in threonine, serine, methionine, cysteine, aspartic acid, asparagine, glutamic acid, glutamine, arginine, and lysine), alkaryl (eg, as in phenylalanine and tryptophan), substituted arylalkyl (eg, as in tyrosine), and heteroarylalkyl (eg, as in histidine).

"Aminocarbonyi" refers to the group —C(O)NRR where each R is independently hydrogen, alkyl, aryl or cycloalkyl, or where the R groups are joined to form an alkylene group.

"Aminocarbonyiamino" refers to the group —NRC(O)NRR where each R is independently hydrogen, alkyl, aryl or cycloalkyl, or where two R groups are joined to form an alkylene group, "Aminocarbonylonxy" refers to the group —OC(O)NRR where each R is independently hydrogen, alkyl, aryl or cycloalky, or where the R groups are joined to form an alkylene group.

"Amino-containing saccharide group" refers to a saccharide group having an amino substituent. Representative amino-containing saccharide include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like."

"ARDS" refers to acute respiratory distress, an ILD

"Aralkyl" or "arylalkyl" refers to an alkyl group, as defined above, substituted with one or more aryl groups, as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

The structures of a few exemplary aryl groups are provided in Table 2.

TABLE 2

Examples of aryl groups

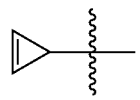

Cyclopropenyl

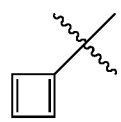

Cyclobuta-1,3-dienyl

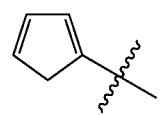 [SMILES: *C1=CC=CC1]

Cyclopenta-1,3-dienyl

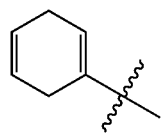

Cyclohexa-1,4-dienyl

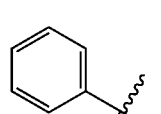

Benzyl

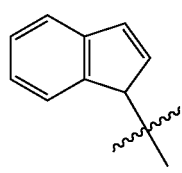 [SMILES: *C1C=Cc2ccccc21]

1H-indenyl

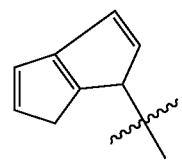 [SMILES: *C1C=CC2=C1CC=C2]

1,6-dihydropentalenyl

TABLE 2-continued

Examples of aryl groups

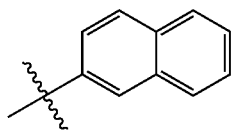 [SMILES: *c1ccc2ccccc2c1]

Napthylenyl

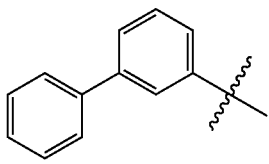 [SMILES: *c1cccc(-c2ccccc2)c1]

1,1'-Biphenyl

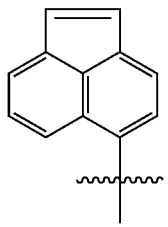 [SMILES: *c1ccc2c3c(cccc13)C=C2]

Acenaphthylenyl

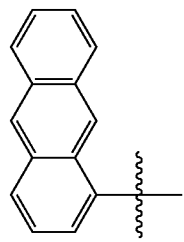 [SMILES: *c1cccc2cc3ccccc3cc12]

Anthracenyl

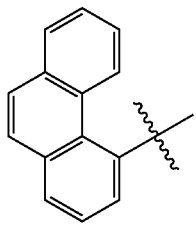 [SMILES: *c1cccc2ccc3ccccc3c12]

Phenanthrenyl

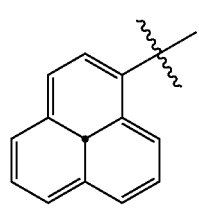

3a¹H-phenalenyl

TABLE 2-continued

Examples of aryl groups

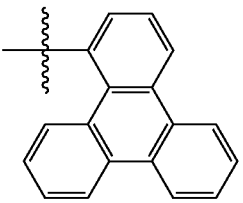 [SMILES: *c1cccc2c3ccccc3c3ccccc3c12]

Triphenylenyl

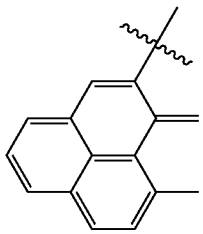 [SMILES: *c1cc2cccc3ccc(C)c(c1=C)c32]

Pyrenyl

"Aryloxy" refers to —O-aryl groups wherein "aryl" is as defined herein.

"Autoimmune disease" or "autoimmune condition" refers an illness that occurs when the body tissues are attacked by its own immune system. Examples of autoimmune disease or conditions include multiple sclerosis, ankylosing spondylitis, Crohn's disease, arthritis, psoriasis, Behçet's disease and psoriatic arthritis.

Azido" refers to the radical —$N_3$.

"BAL" refers to Bronchoalveolar lavage also known as bronchoalveolar washing.

"BALF refers to BAL fluid.

"Carbohydrate" means a mono-, di-, tri-, or polysaccharide, wherein the polysaccharide can have a molecular weight of up to about 20,000, for example, hydroxypropylmethylcellulose or chitosan. "Carbohydrate" also encompasses oxidized, reduced or substituted saccharide monoradical covalently attached to the anhydropyrimidine (eg, anhydrothymidine or anhydrouridine), or derivative thereof any atom of the saccharide moiety, eg, via the aglycone carbon atom, The "mono-, di-, tri-, or polysaccharide" can also include amino-containing saccharide groups. Representative "carbohydrate" include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose-, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. The saccharides can be either in their open, r pyranose or furanose forms.

"Carboxyl" refers to the radical —C(O)OH.

"CHP" refers to chronic hypersensitivity pneumonitis, an ILD.

"CTD-ILD" refers to connective tissue disease-associated ILD.

"Cyano" refers to the radical —CN.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rinds, including fused and bridged ring systems, which optionally can be substituted with from 1 to 3 alkyl groups, Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"FVC" refers to forced vital capacity.

"Heterocycloalkyl" refers to a stable heterocyclic non-aromatic ring and fused rings containing one or more heteroatoms independently selected from N, O and S. A fused heterocyclic ring system may include carbocyclic rinds and need only include one heterocyclic ring. Examples of heterocyclic rings include, but are not limited to, piperazinyl, homopiperazinyl, piperidinyl and morpholinyl.

The structures of a few exemplary heterocyclyls are shown in Table 3.

TABLE 3

Examples of heterocyclyls

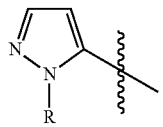

Substituted Pyrazolyl

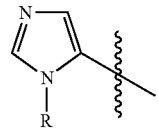

Substituted Imidazole

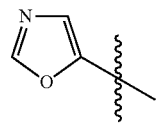 [SMILES: *c1cnco1]

Oxazolyl

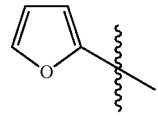 [SMILES: *c1ccco1]

Furanyl

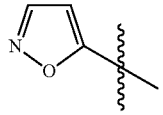

Isoxazolyl

TABLE 3-continued

Examples of heterocyclyls

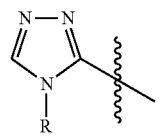

Substituted 1,2,4 Triazolyl

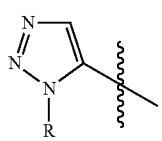

Substituted 1,2,3 Triazolyl

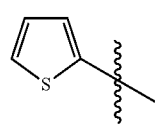 [SMILES: *c1cccs1]

Thiophenyl

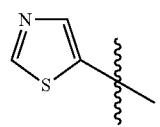 [SMILES: *c1cncs1]

Thiazolyl

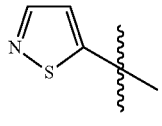

Isothiazolyl

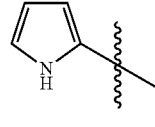 [SMILES: *c1ccc[nH]1]

Pyrrolyl

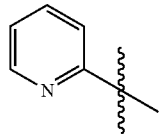 [SMILES: *c1ccccn1]

Pyridinyl

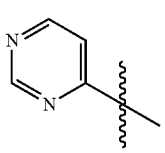 [SMILES: *c1ccncn1]

Pyrimidinyl

TABLE 3-continued

Examples of heterocyclyls

Pyrazinyl

Pyranyl

Tetrazolyl

"Halo" or "halogen" refers to fluoro, chloro, bromo and iodo. Halo groups can be either fluoro or chloro.

"HDL" refers to high density lipoprotein.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, eg heteroalkyl, cycloalkyl, eg heterocycloalkyl, aryl, eg heteroaryl, cycloalkenyl, eg, heterocycloalkenyl, cycloheteroalkenyl, eg, heterocycloheteroalkenyl and the like having from 1 to 5, and particularly from 1 to 3 heteroatoms. A heteroatom is any atom other than carbon or hydrogen and is typically, but not exclusively, nitrogen, oxygen, sulfur, phosphorus, boron, chlorine, bromine, or iodine. An unsubstituted heteroatom refers to a pendant heteroatom such as an amine, hydroxyl and thiol. A substituted heteroatom refers to a heteroatom that is other than a pendant heteroatom.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group can be a 5-20 membered heteroaryl, or 5-10 membered heteroaryl. Particular heteroaryl groups are those derived from thiophen, pyrrole, benzothiophene, benzofuran, indole, pyridine, quinoline, imidazole, oxazole and pyrazine.

"Hydroxyl" refers to the radical —OH.

"IIP" refers to unclassifiable idiopathic interstitial pneumonia.

"ILDs" refers interstitial lung disease.

"I-PAF" refers to interstitial pneumonia with autoimmune features.

"IPF" refers to Interstitial pulmonary fibrosis, an ILD.

"i SIP" refers to idiopathic non-specific interstitial pneumonia, an ILD.

"KO" refers to knockout as used in the phrase knockout animals.

"MCD" refers to methionine-choline deficient diet

"Nitro" refers to the radical —NO$_2$.

"Peptide" refers to a polyamino acid containing up to 2, 5, 10, or about 100 amino acid residues.

"Polypeptide" means polyamino acid containing from about 100 amino acid units to about 1,000 amino acid units, from about 100 amino acid units to about 750 amino acid units, or from about 100 amino acid units to about 500 amino acid units.

"RA-ILD" refers to rheumatoid arthritis-ILD.

"ROP refers to an eye condition in infant's retinopathy of prematurity.

"SEM" refers to standard error of the mean

"Side-effect" means an undesirable adverse consequence of drug administration such as mucositis associated with administration of cancer therapy.

"SSc" refers to systemic sclerosis, an ILD.

"Stereoisomer" as it relates to a given compound is well understood in the art, and refers to another compound having the same molecular formula, wherein the atoms making up the other compound differ in the way they are oriented in space, but wherein the atoms in the other compound are like the atoms in the given compound with respect to which atoms are joined to which other atoms (eg an enantiomer, a diastereomer, or a geometric isomer). For example, Morrison and Boyd, Organic Chemistry, 1983, 4th ed., Allyn and Bacon, Inc., Boston, MA, p123.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, aralkyl, azido, carboxyl, cyano, cycloalkyl, substituted cycloalkyl, halogen, hydroxyl, imidate, keto, nitro, thioalkoxy, substituted thioalkoxy, thioaryloxy, thioketo, thiol, alkylthio, (substituted alkyl)thio, arylthio, (substituted aryl)thio, alkyl-S(O)—, aryl-S(O)—, alkyl-S(O)$_2$— and aryl-S(O)$_2$. Typical substituents include, but are not limited to, —X, —R$^8$ (with the proviso that R$^8$ is not hydrogen), —O—, =O, —OR$^8$, —SR$^8$, —S$^-$, =S, —NR$^8$R$^9$, =NR$^3$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^8$, —OS(O)$_2$O$^-$, —OS(O)$_2$R$^8$, —P(O)(O—)$_2$, —P(O)(OR$^8$)(O$^-$), —OP(O)(OR$^8$)(OR$^9$), —C(O)R$^8$, —C(S)R$^8$, —C(O)OR$^8$, —C(O)NR$^8$R$^9$, —C(O)O$^-$, —C(S)OR$^8$, —NR$^{10}$C(O)NR$^8$R$^9$, —NR$^{10}$C(S)NR$^8$R$^9$, —NR$^{11}$C(NR$^{10}$)NR$^8$R$^9$ and —C(NR$^{10}$)NR$^8$R$^9$, where X is independently a halogen.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group.

"SSc-ILD" refers to systemic sclerosis-ILD.

"T2D" refers to type 2 diabetes.

"TG" refers to transgenic

"Thioalkoxy" refers to the group —S-alkyl.

"Thioaryloxy" refers to the group —S-aryl.

"Thiaketo" refers to the group =S.

"Thiol" refers to the group —SH.

"UR" refers to uridine.

"UPase (Uridine phosphorylase)" refers in enzymology to a phosphorylase (EC 2.4.2.3) that catalyzes the chemical reaction: uridine+phosphate→uracil+alpha-D-ribose 1-phosphate. The two substrates of this enzyme are uridine and phosphate, whereas its two products are uracil and alpha-D-ribose 1-phosphate. This enzyme belongs to the family of glycosyltransferases, specifically the pentosyltransferases. The systematic name of this enzyme class is uridine phosphate alpha-D-ribosyltransferase. Other names in common use include pyrimidine phosphorylase, UrdPase, UPH, and UPase. This enzyme participates in pyrimidine metabolism.

"Uridine Supplement" refers to either a formulated product containing UR or a formulated product containing a UR precursor such as UR monophosphate or acetylated UR that converts to UR in the body. The formulated product could be a solution, a capsule, a tablet or a cream. The product could be administered po, ip, sc, or iv. The UR supplement could be administered as part of a more complex mixture such as a nutritional supplement.

ip, po and sc are intraperitoneal, oral or subcutaneous dosing, respectfully. H&E is Haematoxylin & Eosin, a dye used to stain tissues. SD is standard deviation. SE is standard error. PBS is phosphate buffered saline. qd. and bid are daily and twice-a-day, respectfully.

One having ordinary skill in the art will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

DETAILED DESCRIPTION

Methods for treating a subject for pulmonary conditions are provided. Aspects of the methods include administering an effective amount of a UR plasma level modulator to a subject. In certain embodiments, the therapy is a 2,2'-anhydropyrimidine, or a derivative thereof. Also provided are compositions for use in practicing the subject methods. The subject methods and compositions find use in a variety of different applications to treat serious pulmonary conditions.

In some instances, anhydronucleosides are employed in combination with UR, a UR pro-drug, or a UR mimetic. Anhydronucleosides are analogs of natural nucleosides, often finding use as intermediates in the synthesis of nucleoside derivatives. They are characterized by having, in addition to the N-glycoside linkage, a covalent linkage either directly or via bridging atoms between the 2', 3', or 5' carbons of the sugar and a carbon, oxygen or nitrogen atom (other than the nitrogen of the glycoside bond) of the base. The anhydropyrimidines are characterized by a pyrimidine base that is covalently linked either directly or via bridging atoms between the 2', 3', or 5' carbons of the sugar and a carbon, oxygen or nitrogen atom (other than the nitrogen of the glycoside bond) of the pyrimidine base.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing the subject invention, the subject methods are described first in greater detail, followed by a review of the various compositions, e.g., formulations and kits, that may find use in the subject methods, as well as a discussion of various representative applications in which the subject methods and compositions find use.

Methods

As summarized above, methods of treating a subject for pulmonary conditions are provided. An aspect of the subject methods is administration to the subject of an effective amount of a UR plasma level modulator. In certain embodiments, the treatment is a 2,2'-anhydropyrimidine, such as a 2,2'-anhydrouridine or analogue/derivative thereof. The UR plasma level modulator, e.g., UR elevation agent, may be used in combination with UR, a UR pro-drug, or UR mimetic. In one embodiment, the UR, UR pro-drug or UR mimetic are administered simultaneously with the UR elevating agent. In yet other embodiments, the UR elevating agent, e.g., an 2,2'-anhydropyrimidine, and the UR, UR pro-drug or UR mimetic are administered sequentially. The UR elevating agent and the UR, UR pro-drug or UR mimetic can be administered at the same time as two separate formulations or are combined into a single composition that is administered to the subject. Regardless of whether the uridine elevating agent and UR plasma level modulator are administered sequentially or simultaneously, or any effective variation thereof, the agents are considered to be administered together or in combination for purposes of the present invention. Routes of administration of the two agents may vary. Representative routes of administration are described below.

In the subject methods, an effective amount of a UR plasma level modulator, e.g., UR elevating agent, is administered to a subject, optionally in combination with one or more of UR, UR pro-drug, or a UR mimetic.

A UR plasma level modulator is an agent that changes the plasma UR level of a subject following administration to the subject. A UR plasma level modulator enhances the plasma UR level in the subject. While the magnitude of any enhancement may vary, in some instances the magnitude of enhancement is 2-fold or greater, such as 5-fold or greater, 10-fold or greater, 15-fold or greater, 20-fold or greater, 25-fold or greater, or 50-fold or greater. A variety of different types of plasma UR level enhancing agents may be employed. Plasma UR level enhancing agents include, but are not limited to, UR and sources thereof, UR precursors as sources thereof, and UR degradation inhibitors, such as UPase inhibitors, UR secretion inhibiting compounds and UR renal transport competitors. Of particular interest are 2,2'-anhydropyrimidines and derivatives thereof that are inhibitors of UPase. UPase (UPh; EC 2.4.2.3) is a member of the pyrimidine nucleoside phosphorylase family of enzymes which catalyzes the phosphorolytic cleavage of the C—N glycoside bond of UR, with the formation of ribose 1-phosphate and uracil. (Pizzorno G, Cao D, Leffert J J, Russell R L, Zhang D, Handschumacher R E, Homeostatic control of uridine and the role of uridine phosphorylase: a biological and clinical update, Biochim Biophys Acta. 2002; 1587(2-3): 133-44), In some instances, the UR elevating agent is 2,2'-anhydropyrimidines or a derivative thereof. In some embodiments, the 2,2'-anhydropyrimidine or derivative thereof is a compound of formula (I):

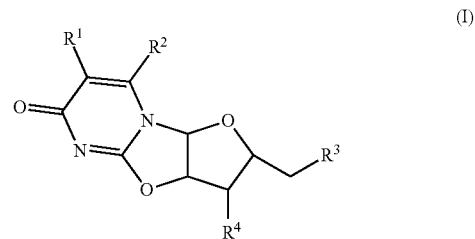

or the pharmaceutically acceptable salts, solvates, hydrates, and prodrug forms thereof, and stereoisomers thereof;

wherein:

each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, hydroxyl, halogen, azido, amino, substituted amino, carbohydrate, nucleic acid, amino acid, peptide, dye, fluorophore and polypeptide.

In certain embodiments, the compound is of formula (I), R', $R^2$, $R^3$ and $R^4$ are independently hydrogen, hydroxyl, heteroatom, $C_1$-$C_{18}$ alkyl, $C_1$-$C_{18}$ substituted alkyl, $C_1$-$C_{18}$ alkenyl, $C_1$-$C_{18}$ acyl, amino, substituted amino, wherein the alkyl, alkenyl or acyl is linear or branched, and optionally substituted with a hydroxyl, an ester and its derivatives, a carboxyl and its derivatives, a cycloalkyl, a heterocycloalkyl, an aryl, a heteroaryl, an aralkyl, a heteroatom, and possibly containing in chain or bridging heteroatoms such as nitrogen, oxygen and sulfur.

Examples of $R^1$ constituents of interest include, but are not limited to: hydrogen; hydroxyl; sulfyhydryl; halogen such as fluorine, chlorine, bromine or iodine, as well as pseudohalogen such as a lower alkylsulfonyl group of 1 to 5 carbons such as methyl-, ethyl-, propyl-, isopropyl-, butyl-, isobutyl-, tert-butyl-, and pentasulfonyl or arylsulfonyl such as benzene, p-toluene, p-nitrobenzenesulfonyl groups; lower alkyl containing 1 to 20 carbons such as methyl, ethyl, propyl, isopropyl, butyl, isobutyl, tert-butyl, pentyl and the like, including substituted lower alkyl such as aminomethyl, hydroxymethyl, methoxy, ethyloxy, propyloxy, benzyloxy, imidate, alkylthio, (substituted alkyl)thio, arylthio, (substituted aryl)thio and the like; lower alkenyl containing 1 to 20 carbons such as vinyl and substituted vinyl, ethynyl and substituted ethynyl, where the substituted vinyl or substituted ethynyl designates substitution of the p position of vinyl or ethynyl by a halogen such as bromine, chlorine, fluorine or iodine, or substitution by an alkyl of 1 to 5 carbon atoms such as methyl, ethyl, propyl, butyl, pentyl and the like, or aralkyl such as benzyl, p-chlorobenzyl, p-nitrobenzyl and the like, or aryl such as phenyl, p-nitrophenyl, p-tolyl, p-anisyl, naphtyl and the like; lower alkanoyl (acyl groups) containing 1 to 20 carbons such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like; lower aryl containing 1 to 20 carbons such as phenyl, p-tolyl, p-chlorophenyl, p-aminophenyl, p-nitrophenyl, p-anisyl and the like; lower aroyl containing 1 to 20 carbons such as benzoyl and naphthoyl, where the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl, pentafluorobenzayl and the like, or another aroyl such as benzyloxybenzoyl and the like; lower aralkyl containing 1 to 20 carbons such as benzyl, benzhydryl, p-chlorobenzyl, m-chlorobenzyl, p-nitrobenzyl, benzyloxybenzyl, pentaflourobenzyl and the like; amino or alkylamino containing 1 to 20 carbons such as a monoalkyl- or monoaralkylamino groups like methylamino, ethylamino, propylamino or benzylamino and the like, dialkylamino such as dimethylamino, diethylamino, dibenzylamino, pyrrolidino, piperidino or molpholino and the like.

Thus, in certain embodiments, $R^1$ is hydrogen, hydroxyl, sulfyhydryl, amino, substituted amino, hydroxymethyl, monomethoxy, halogen, pseudohalogen, or a lower hydrocarbon (which hydrocarbon can be substituted or unsubstituted) containing from 1 to 20 atoms. In a particular embodiment, $R^1$ is a lower hydrocarbon selected from alkyl, substituted alkyl, alkenyl, alkanoyl, aryl, aroyl, aralkyl, or alkylamino. In a particular embodiment, $R^1$ is a lower hydrocarbon substituted with alkoxy, substituted alkoxy, imidate, arylthio, or (substituted aryl) thio. In other embodiments, $R^1$ is a lower alkyl selected from methyl, ethyl, propyl, isopropyl, butyl, isobutyl, tert-butyl and pentyl. In other embodiments, $R^1$ is a lower alkenyl selected from vinyl, substituted vinyl, ethynyl, or substituted ethynyl. In other embodiments, $R^1$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, $R^1$ is lower aryl selected from phenyl, p-tolyl, p-chlorophenyl, p-aminophenyl, p-nitrophenyl, p-anisyl. In yet other embodiments, $R^1$ is a lower aroyl selected from benzoyl and naphthoyl. In other embodiments, $R^1$ is a lower aralkyl selected from benzyl, benzhydryl, p-chlorobenzyl, m-chlorobenzyl, p-nitrobenzyl, benzyloxybenzyl, or pentaflourobenzyl. In certain other embodiments, $R^1$ is a lower alkylamino is selected from monoalkylamino, monoaralkylamino, dialkylamino, diaralkylamino, and benzylamino.

Compounds of interest include, but are not limited to, those of formula (I) where $R^1$ is selected from hydrogen, fluorine, trifluoromethyl, methyl, ethyl, propyl, butyl, isopropyl, isobutyl, acetyl, propionyl, butyryl, 2-bromovinyl, phenyl, benzyl, benzoyl, benzyloxybenzyl, benzylamino, alkyloxyalkyl, benzyloxyalkyl, imidatealkyl, arylthio, and (substituted aryl) thio. Thus, in certain embodiments, the compound is of formula (I), and $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH═CH, phenyl, benzyl, benzoyl, benzyloxybenzyl, benzyl-NH—, $CH_3CH_2OCH_2$, benzyl-O—$CH_2$, $CH_3OCH_2$, $CH_3C(NH)$—O—$CH_2$, or $CH_3$-phenyl-O—$CH_2$.

Examples of $R^2$ constituents of interest include, but are not limited to: hydrogen; hydroxyl; sulfyhydryl; halogen such as fluorine, chlorine, bromine or iodine, as well as pseudohalogen such as a lower alkylsulfonyl group of 1 to 5 carbons such as methyl-, ethyl-, propyl-, isopropyl-, butyl-, isobutyl-, tert-butyl-, and pentasulfonyl or arylsulfonyl such as benzene, p-toluene, p-nitrobenzenesulfonyl groups; lower alkyl containing 1 to 20 carbons such as methyl, ethyl, propyl, isopropyl, butyl, isobutyl, tert-butyl, pentyl and the like, including substituted lower alkyl such as aminomethyl, hydroxymethyl, methoxy, ethyloxy, propyloxy, and the like; lower alkenyl containing 1 to 20 carbons such as vinyl and substituted vinyl, ethynyl and substituted ethynyl, where the substituted vinyl or substituted ethynyl designates substitution of the ß position of vinyl or ethynyl by a halogen such as bromine, chlorine, fluorine or iodine, or substitution by an alkyl of 1 to 5 carbon atoms such as methyl, ethyl, propyl, butyl, pentyl and the like, or aralkyl such as benzyl, p-chlorobenzyl, p-nitrobenzyl and the like, or aryl such as phenyl, p-nitrophenyl, p-tolyl, p-anisyl, naphtyl and the like; lower alkanoyl (acyl groups) and esters thereof of a main chain containing 1 to 20 carbons such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like; lower aryl containing 1 to 20 carbons such as phenyl, p-tolyl, p-chlorophenyl, p-aminophenyl, p-nitrophenyl, p-anisyl and the like; lower aroyl containing 1 to 20 carbons such as benzoyl and naphthoyl, where the aromatic group may be additionally substituted by alkyl, alkoxy, halo, or nitro moieties such as p-tolnoyl, p-anisoyl, p-chlorobenzoyl, p-nitrobenzayl or 2,4-dinitrobenzoyl, pentafluorobenzoyl and the like, or another aroyl such as benzyloxybenzoyl and the like; lower aralkyl containing 1 to 20 carbons such as benzyl, benzhydryl, p-chlorobenzyl, m-chlorobenzyl, p-nitrobenzyl, benzyloxybenzyl, pentaflourobenzyl and the like; lower aryloxy containing 1 to 20 carbons such as phenyloxy (ie, O-phenyl), benzyloxy (ie, O-benzyl), benzhydryloxy (ie, O-benzylhydryl), p-chlorobenzyloxy (ie, O-(p-chlorobenzyl)), m-chlorobenzyloxy (ie, O-(m-chlorobenzyl)), p-nitrobenzyloxy (ie, O-(p-nitrobenzyl)), (4-benzyloxybenzyl)-oxy (ie, O-benzyloxybenzyl), or pentaflourobenzyloxy (ie, O-pentaflourobenzyl); esters of aryloxys, such as lower aroyloxy (ie, O-aroyl) containing 1 to 20 carbons such as benzoyloxy (ie, O-benzoyl), diphenylacetyloxy (ie, O-diphenylacetyl), p-chlorobenzoyloxy (ie, O-(p-chlorobenzoyl)), m-chlorobenzoyloxy (ie, O-(m-chlorobenzoyl)), p-nitrobenzoyloxy (ie, O-(p-nitrobenzoyl)), (4-benzyloxybenzoyl)-oxy (ie, O-benzyloxybenzoyl), or pentaflourobenzoyloxy (ie, O-pentaflourobenzoyl); amino or alkylamino containing 1 to 20 carbons such as a monoalkyl- or monoaralkylamino groups like methylamino, ethylamino, propylamino or benzylamino and the like, dialkylamino such as dimethylamino, diethylamino, dibenzylamino, pyrrolidine, piperidino or molpholino and the like.

Thus, in certain embodiments, $R^2$ is hydrogen, hydroxyl, sulfyhydryl, amino, hydroxymethyl, monomethoxy, halogen, pseudohalogen, or a lower hydrocarbon (which hydrocarbon can be substituted or unsubstituted) containing from 1 to 20 atoms, and esters thereof. In a particular embodiment, $R^2$ is a lower hydrocarbon selected from alkyl, alkenyl, alkanoyl, aryl, aroyl, aryloxy, aroyloxy, aralkyl, or alkylamino. In other embodiments, $R^2$ is a lower alkyl selected from methyl, ethyl, propyl, isopropyl, butyl, isobutyl, tert-butyl and pentyl. In other embodiments, $R^2$ is a lower alkenyl selected from vinyl, substituted vinyl, ethynyl, or substituted ethynyl. In other embodiments, $R^2$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, $R^2$ is lower aryl selected from phenyl, p-tolyl, p-chlorophenyl, p-aminophenyl, p-nitrophenyl, p-anisyl. In yet other embodiments, $R^2$ is a lower aroyl selected from benzoyl and naphthoyl. In other embodiments, $R^2$ is a lower aralkyl selected from benzyl, benzhydryl, p-chlorobenzyl, m-chlorobenzyl, p-nitrobenzyl, benzyloxybenzyl, or pentaflourobenzyl. In other embodiments, $R^2$ is a lower aryloxy selected from phenyloxy, benzyloxy, benzhydryloxy, p-chlorobenzyloxy, m-chlorobenzyloxy, p-nitrobenzyloxy, (4-benzyloxybenzyl)-oxy, or pentaflourobenzyloxy. In other embodiments, $R^2$ is a lower aroyloxy selected from benzoyloxy, diphenylacetyloxy, p-chlorobenzoyloxy, m-chlorobenzoyloxy, p-nitrobenzoyloxy, (4-benzyloxybenzoyl)-oxy, or pentaflourobenzayloxy. In certain other embodiments, $R^2$ is a lower alkylamino is selected from rnonoalkylamino, monoaralkylamino, dialkylamino, and diaralkylamino. Thus, in certain embodiments, $R^2$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Compounds of interest include, but are not limited to, those of formula (I) where $R^2$ is selected from hydrogen, fluorine, trifluoromethyl, methyl, ethyl, propyl, butyl, isopropyl, isobutyl, acetyl, propionyl, butyryl, 2-bromovinyl, phenyl, phenyloxy, benzyl, benzoyl, benzoyloxy and benzyloxybenzyl. Thus, in certain embodiments, the compound is of formula (I), and $R^2$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzoyl, benzoyloxy, or benzyloxybenzyl.

In specific embodiments of interest, the compound is of formula (I), and $R^2$ is hydrogen, hydroxyl, or an O-linked substituent. This includes compounds of formula (I), where $R^2$ is H, OH or $C_6H_5C(O)O$.

Examples of $R^3$ of interest include, but are not limited to: hydrogen; hydroxyl; azido; sulfyhydryl; halogen; pseudohalogen; lower alkyl containing 1 to 20 carbons such as methyl, ethyl, propyl, isopropyl, butyl, isobutyl, tert-butyl, pentyl and the like, including a substituted lower alkyl such as aminomethyl, hydroxymethyl, methoxy, ethyloxy, propyloxy, and the like; lower alkanoyl (acyl) including esters thereof of a main chain of 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like; lower aryl such as phenyl, p-nitrophenyl, p-tolyl, p-anisyl, naphtyl and the like; lower aroyl (acyl radical of an aromatic acid) of 1 to 20 carbons such as benzoyl and naphthoyl, where the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl, pentafluorobenzoyl and the like; lower aryloxy of 1 to 20 carbons such as phenyloxy, benzyloxy, benzhydryloxy, p-chlorobenzyloxy, m-chlorobenzyloxy, p-nitrobenzyloxy, (4-benzyloxybenzyl)-oxy, or pentaflourobenzyloxy and the like; as well as esters of aryloxys, such as lower aroyloxy (O-aroyls) of 1 to 20 carbons such as benzoyloxy, diphenylacetyloxy, p-chlorobenzoyloxy, m-chlorobenzoyloxy, p-nitrobenzoyloxy, (4-benzyloxybenzoyl)-oxy, or pentaflourobenzoyloxy and the like. $R^3$ may also be adamantoyl, or substituted adamantoyl.

Thus, in certain embodiments, $R^3$ is hydrogen, hydroxyl, azido, sulfyhydryl, hydroxymethyl, halogen, or pseudohalogen. In other embodiments, $R^3$ is a lower hydrocarbon selected from alkyl, alkanoyl, aryl, aroyl, aryloxy, aroyloxy, or aralkyl. In other embodiments, $R^3$ is a lower alkyl selected from methyl, ethyl, propyl, isopropyl, butyl, isobutyl, tert-butyl and pentyl. In other embodiments, $R^3$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, $R^3$ is a lower aryl selected from phenyl, p-tolyl, p-chlorophenyl, p-aminophenyl, p-nitrophenyl, p-anisyl and the like. In other embodiments, $R^3$ is a lower aroyl selected from benzoyl and naphthoyl. In yet other certain embodiments, $R^3$ is a lower aralkyl selected from benzyl, benzhydryl, p-chlorobenzyl, m-chlorobenzyl, p-nitrobenzyl, benzyloxybenzyl, or pentaflourobenzyl. In other embodiments, $R^3$ is a lower aryloxy selected from phenyloxy, benzyloxy, benzhydryloxy, p-chlorobenzyloxy, m-chlorobenzyloxy, p-nitrobenzyloxy, (4-benzyloxybenzyl)-oxy, or pentaflourobenzyloxy. In other embodiments, $R^3$ is a lower aroyloxy selected from benzoyloxy, diphenylacetyloxy, p-chlorobenzoyloxy, m-chlorobenzoyloxy, p-nitrobenzoyloxy, (4-benzyloxybenzoyl)-oxy, or pentaflourobenzoyloxy. Thus, in certain embodiments, $R^3$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Compounds of interest are those of formula (I) where $R^3$ is hydrogen, hydroxyl, halogen, azido, or an O-linked substituent. This includes compounds of formula (I) where $R^3$ is selected from hydrogen, hydroxyl, n-butoxy, isobutyloxy, t-butyloxy, phenyloxy, benzyloxy, benzoyloxy, and pentafluorobenzoyloxy. Thus, in certain embodiments, the compound is of formula (I), and $R^3$ is selected from H, OH, $CH_3CH_2CH_2CH_2O$, $(CH_3)_2CH_2CH_2O$, $(CH_3)_3CO$, $C_6H_5O$, benzoyloxy, and pentafluorobenzoyloxy.

In specific embodiments of interest, the compound is of formula (I), where $R^3$ is H, OH, F, Cl, Br, I, $N_3$, or $C_6H_5C(O)O$. Of special interest is a compound of formula (I), where $R^3$ is OH, or O-acyl (for example, an ester such as $C_6H_5C(O)O$).

Examples of $R^4$ include but are not limited to: hydrogen; hydroxyl; sulfhydryl; halogen such as fluorine, chlorine, bromine or iodine; amino or lower alkylamino. $R^4$ also is exemplified by lower alkyl, with acyl groups which may be lower alkanoyl groups of 1 to 7 carbon atoms such as formyl, acetyl, propionyl, isopropionyl, butyryl, isobutyryl, tert-butyryl and the like, and esters thereof. Thus, $R^4$ can also be aroyl (and esters thereof such as O-linked aroyls, ie, O-arolys or arolyoxy) such as benzoyl and naphthoyl wherein the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl and the like. Accordingly, in certain embodiments, $R^4$ can not only be hydrogen or hydroxyl, but also an O-acyl, alkoxy, alkoxycarbonyl, alkoxycarbonylamino, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Thus, in certain embodiments, $R^4$ is hydrogen; hydroxyl; sulfhydryl; halogen, amino aminomethyl, or aminodimethyl. In other embodiments, $R^4$ is a lower alkyl, acyl, aroyl, or aroyloxy. This includes a specific embodiment, where the compound of formula (I) is one where $R^4$ is hydrogen, flourine, hydroxyl, amino, aminomethyl, aminodimethyl, t-butyloxy, phenyloxy or benzoyloxy (for example, a compound of formula (I), where $R^4$ is H, F, OH, $NH_2$, $NHCH_3$, $N(CH_3)_2$, $(CH_3)_3CO$, $C_8H_5O$ or $C_6H_5C(O)O$).

Compounds of particular interest are those of formula (I) where $R^4$ is hydrogen, hydroxyl, or an O-linked substituent, In specific embodiments, the compound is of formula (I), where $R^4$ is H, OH or $C_6H_5C(O)O$. Of special interest is a compound of formula (I), where $R^4$ is OH, or O-acyl (for example, an ester such as $C_6H_5C(O)O$).

Of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzoyl, benzoyloxy, or benzyloxybenzyl, and where $R^3$ and $R^4$ are each hydroxyl. These include the compounds: 2,2'-anhydrouridine; 2,2'-anhydro-5-fluorouridine; 2,2'-anhydro-5-trifluoromethyluridine; 2,2'-anhydro-5-methyluridine; 2,2'-anhydro-5-ethyluridine; 2,2'-anhydro-5-propyluridine; 2,2'-anhydro-5-isopropyluridine; 2,2'-anhydro-5-isobutyluridine; 2,2'-anhydro-5-methylacyluridine; 2,2'-anhydro-5-propylacyluridine; 2,2'-anhydro-5-(2-bromovinyl)-uridine; 2,2'-anhydro-5-phenylluridine; 2,2'-anhydro-5-benzyluridine; 2,2'-anhydro-5-benzyoluridine; and 2,2'-anhydro-5-(benzyloxybenzyl)-uridine. Of special interest is 2,2'-anhydro-5-methyluridine, or the pharmaceutically acceptable salts, solvates, hydrates, and prodrug forms thereof, and stereoisomers thereof.

Additional compounds of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzoyloxy, or benzyloxybenzyl, and where $R^3$ is hydroxyl, and $R^4$ is benzayloxy. These include the compounds: 3'-O-benzoyl-2,2'-anhydrouridine; 3'-O-benzoyl-2,2'-anhydro-5-fluorouridine; 3'-O-benzoyl-2,2'-anhydro-5-trifluoromethyluridine; 3'-O-benzoyl-2,2'-anhydro-5-methyluridine; 3'-O-benzoyl-2,2'-anhydro-5-ethyluridine; 3'-O-benzoyl-2,2'-anhydro-5-propyluridine; 3'-O-benzoyl-2,2'-anhydro-5-isopropyluridine; 3'-O-benzoyl-2,2'-O-anhydro-5-isobutyluridine; 3'-O-benzoyl-2,2'-anhydro-5-methylacyluridine; 3'-O-benzoyl-2,2'-anhydro-5-propylacyluridine; 3'-O-benzoyl-2,2'-anhydro-5-(2-bromovinyl)-uridine; 3'-O-benzoyl-2,2'-anhydro-5-phenylluridine; 3'-O-benzoyl-2,2'-anhydro-5-benzyluridine; 3'-O-benzoyl-2,2'-anhydro-5-benzyoluridine; and 3'-O-benzoyl-2,2'-anhydro-5-(benzyloxybenzyl)-uridine. Of specific interest is 3'-O-benzoyl-2,2'-anhydro-5-methyluridine, or the pharmaceutically acceptable salts, solvates, hydrates, and prodrug forms thereof, and stereoisomers thereof.

Also of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzoyloxy, or benzyloxybenzyl, and where $R^3$ is benzoyloxy, and $R^4$ is hydroxyl. These include the compounds: 5-O-benzoyl-2,2'-anhydrouridine; 5'-O-benzoyl-2,2'-anhydro-5-fluorouridine; 5'-O-benzoyl-2,2'-anhydro-5-trifluoromethyluridine; 5'-O-benzoyl-2,2'-anhydro-5-methyluridine; 5'-O-benzoyl-2,2'-anhydro-5-ethyluridine; 5-O-benzoyl-2,2'-anhydro-5-propyluridine; 5'-O-benzoyl-2,2'-anhydro-5-isopropyluridine; 5'-O-benzoyl-2,2'-O-anhydro-5-isobutyluridine; 5'-O-benzoyl-2,2'-anhydro-5-methylacyluridine; 5'-O-benzoyl-2,2'-anhydro-5-propylacyluridine; 5'-O-benzoyl-2,2'-anhydro-5-(2-bromovinyl)-uridine; 5'-O-benzoyl-2,2'-anhydro-5-phenylluridine; 5-O-benzoyl-2,2'-anhydro-5-benzyluridine; 5-O-benzoyl-2,2'-anhydro-5-benzyoluridine; and 5-O-benzoyl-2,2'-anhydro-5-(benzyloxybenzyl)-uridine. Of specific interest is 5'-O-benzoyl-2,2'-anhydro-5-methyluridine, or the pharmaceutically acceptable salts, solvates, hydrates, and prodrug forms thereof, and stereoisomers thereof.

The 2,2'-anhydropyrimidine compounds of the invention may be in compositions that contain single stereoisomers, mixtures of stereoisomers, as well various derivatives thereof that can occur as equilibrium mixtures of tautomers. For instance, 2,2'-anhydropyrimidines according to formula (I) include four stereo centers with respect to the furano ring, which includes the α and β anomers, and the L or D mirror image configurations. Examples of stereoisomers of the 2,2'-anhydropyrimidine compounds of the invention are the β-D-isomer, β-L-isomer, α-D-isomer, and α-L-isomer, as well as tautomers and mixtures including α,β-D-isomers, α,β-L-isomers, α-DL-isomers, and β-DL-isomers. Thus, in one embodiment, compositions are provided that consists essentially of a stereoisomer of a 2,2'-anhydropyrimidine that is a β-D-isomer, β-L-isomer, α-D-isomer, or an α-L-isomer. Stereoisomers exhibiting improved activity on a molar basis or improved specificity with respect to interfering with cancer therapy efficacy are of special interest.

Stereoisomers of particular interest include: 2,2'-anhydro-1-(β-D-arabinofuranosyl)uracil; 2,2'-anhydro-1-(β-D-arabinofuranosyl)-5-fluorouracil; 2,2'-anhydro-1-(β-D-arabinofuranosyl)-5-trifluoromethyluracil; 2,2'-anhydro-1-(β-D-arabinofuranosyl)-5-methyluracil; 2,2'-anhydro-1-(β-D-arabinofuranosyl)-5-ethyluracil; 2,2'-anhydro-1-(β-D-arabinofuranosyl)-5-n-propyluracil; 2,2'-anhydro-1-(β-D-arabinofuranosyl)-5-isopropyluracil; 2,2'-anhydro-1-(β-D-arabinofuranosyl)-5-isobutyluracil; 2,2'-anhydro-1-(β-D-arabinofuranosyl)-5-methyacyluracil; 2,2'-anhydro-1-(β-D-arabinofuranosyl)-5-propylacyluracil; 2,2'-anhydro-1-(β-D-arabinafuranosyl)-5-(2-bromovinyl)uracil; 2,2'-anhydro-1-(β-D-arabinofuranosyl)-5-phenyluracii; 2,2'-anhydro-1-(β-D-arabinofuranosyl)-5-benzyluracil; 2,2'-anhydro-1-(β-D-arabinofuranosyl)-5-benzyouracil; and 2,2'-anhydro-1-(β-D-arabinofuranosyl)-5-(β-benzyoxybenzyl)uracil. Further stereoisomers of interest include: 3'-O-benzoyl-2,2'-anhydro-1-(β-D-arabinofuranosyl)uracil; 3'-O-benzoyi-2,2'-anhydro-1-(β-D-arabinofuranosyl)-5-fluororacii; 3'-O-benzoyl-2,2'-anhydro-1-(β-D-arabinofuranosyl)-5-trifluoromethyluracil; 3'-O-benzoyl-2,2'-anhydro-1-(β-D-arabinofuranosyl)-5-methyluracil; 3'-O-benzoyl-2,2'-anhydro-1-(β-D-arabinofuranosyl)-5-ethyluracil; 3'-O-benzoyl-2,2'-anhydro-1-(β-D-arabinofuranosyI)-5-n-propyluracil; 3'-O-benzoyl-2,2'-anhydro-1-(β-D-arabinofuranosyl)-5-isopropyluracil; 3'-O-benzoyl-2,2'-anhydro-1-(β-D-arabinofuranosyl)-5-isobutyluracil; 3'-O-benzoyl-2,2'-anhydro-1-(β-O-arabinofuranosyl)-5-methyacyluracil; 3'-O-benzoyl-2,2'-anhydro-1-(β-D-arabinofuranosyl)-5-propylacyluracil; 3'-O-benzoyl-2,2'-anhydro-1-(β-D-arabinofuranosyl)-5-(2-bromovinyl)uracil; 3'-O-benzoyl-2,2'-anhydro-1-(β-D-arabinofuranosyl)-5-phenyluracil; 3'-O-benzoyl-2,2'-anhydro-1-(β-D-arabinofuranosyl)-5-benzyluracil; 3-O-benzoyl-2,2'-anhydro-1-(β-D-arabinofuranosyl)-5-benzyouracil; and 3'-O-benzoyl-2,2'-anhydro-1-(β-D-arabinofuranosyl)-5-(3-benzyoxybenzyl)uracil. Additional stereoisomers of interest include: 5'-O-benzoyl-2,2'-anhydro-1-(β-D-arabinofuranosyl)uracil; 5'-O-benzoyl-2,2'-anhydro-1-(β-D-arabinofuranosyl)-5-fluorouracil; 5'-O-benzoyl-2,2'-anhydro-1-(β-D- arabinafuranosyl)-5-trifluoromethyluracil; 5'-O-benzoyl-2,2'-anhydro-1-(β-D-arabinofuranosyl)-5-methyluracil; 5'-O-benzoyl-2,2'-anhydro-1-(β-D-arabinofuranosyl)-5-ethyluracil; 5'-O-benzoyl-2,2'-anhydro-1-(β-D-arabinofuranosyl)-5-n-propyluracil; 5'-O-benzoyl-2,2'-anhydro-1-(β-D-arabinofuranosyl)-5-isopropyluracil; 5'-O-benzoyl-2,2'-anhydro-1-(β-D-arabinofuranosyl)-5-isobutyluracil; 5'-O-benzoyl-2,2'-anhydro-1-(β-D-arabinofuranosyl)-5-methyacyluracil; 5'-O-benzoyl-2,2'-anhydro-1-(β-D-arabinofuranosyl)-5-propylacyluracil; 5'-O-benzoyl-2,2'-anhydro-1-(β-D-arabinofuranosyl)-5-(2-bromovinyl)uracil; 5'-O-benzoyl-2,2'-anhydro-1-(β-D-arabinofuranosyl)-5-phenyluracil; 5'-O-benzoyl-2,2'-anhydro-1-(β-D-arabinofuranosyl)-5-benzyluracil; 5'-O-benzoyl-2,2'-anhydro-1-(β-D-arabinofuranosyl)-5-benzyoluracil; and 5'-O-benzoyl-2,2'-anhydro-1-(β-D-arabinofuranosyl)-5-(3-benzyoxybenzyl)uracil.

Examples of other analogs or derivatives of the 2,2'-anhydropyrimidines of the invention, and stereoisomers thereof include: 3'-O-acetyl-2,2'-anhydro-5-propyluridine (3'-O-acetyl-2,2'-anhydro-1-(β-D-arabinofuranosyl)-5-propyluracil); and 3'-O-acetyl-2,2'-anhydro-5-isopropyluridine (3'-O-acetyl-2,2'-anhydro-1-(β-D-arabinofuranosyl)-5-isopropyluracil); as well as the 2,2'-anhydrocytidines, and analogs and derivatives thereof, of which the stereoisomer 2,2'-anhydro-1-(β-D-arabinofuranosyl)cytosine is one example.

As noted above, stereoisomers and the various 2,2'-anhydropyrimidines of particular interest are those which exhibit improved activity on a molar basis, or improved specificity with respect to not interfering with cancer therapy efficacy. Such compounds can be readily selected for this purpose by comparing against a matrix of compounds of particular interest, such as those illustrated in Table 1 (where the compound is of formula (I)).

TABLE 1

The compound is of formula (I)

| Compound | Stereoisomer | $R^1$ | $R^2$ | $R^3$ | $R^4$ |
|---|---|---|---|---|---|
| I-a | β-D-isomer | H | H | OH | OH |
| I-b | β-D-isomer | $CH_3$ | H | OH | OH |
| I-c | β-D-isomer | $CH_3CH_2$ | H | OH | OH |
| I-d | β-D-isomer | $CH_3CH_2CH$ | H | OH | OH |
| I-e | β-D-isomer | $BrCH=CH$ | H | OH | OH |
| I-f | β-D-isomer | $C_6H_5CH_2$ | H | OH | OH |
| I-g | β-D-isomer | H | H | $C_6H_5C(O)O$ | OH |
| I-h | β-D-isomer | $CH_3$ | H | $C_6H_5C(O)O$ | OH |
| I-i | β-D-isomer | $CH_3CH_2$ | H | $C_6H_5C(O)O$ | OH |
| I-j | β-D-isomer | $CH_3CH_2CH$ | H | $C_6H_5C(O)O$ | OH |
| I-k | β-D-isomer | $BrCH=CH$ | H | $C_6H_5C(O)O$ | OH |
| I-l | β-D-isomer | $C_6H_5CH_2$ | H | $C_6H_5C(O)O$ | OH |
| I-m | β-D-isomer | $F-C_6H_5CH_2$ | H | OH | OH |
| I-n | β-D-isomer | $NO_2-C_6H_5CH_2$ | H | OH | OH |
| I-o | β-D-isomer | $NH_2-C_6H_5CH_2$ | H | OH | OH |
| I-p | β-D-isomer | $Cl-C_6H_5CH_2$ | H | OH | OH |
| I-q | β-D-isomer | Alkyl-$C_6H_5CH_2$ | H | OH | OH |
| I-r | β-D-isomer | Methoxy-$C_6H_5CH_2$ | H | OH | OH |
| I-s | β-D-isomer | Thiol-$C_6H_5CH_2$ | H | OH | OH |
| I-t | β-D-isomer | $F-C_6H_5CH_2$ | H | $C_6H_5C(O)O$ | OH |
| I-u | β-D-isomer | $NO_2-C_6H_5CH_2$ | H | $C_6H_5C(O)O$ | OH |
| I-v | β-D-isomer | $NH_2-C_6H_5CH_2$ | H | $C_6H_5C(O)O$ | OH |
| I-w | β-D-isomer | $Cl-C_6H_5CH_2$ | H | $C_6H_5C(O)O$ | OH |
| I-x | p-D-isomer | Alkyl-$C_6H_5CH_2$ | H | $C_6H_5C(O)O$ | OH |
| I-y | β-D-isomer | Methoxy-$C_6H_5CH_2$ | H | $C_6H_5C(O)O$ | OH |
| I-z | β-D-isomer | Thiol-$C_6H_5CH_2$ | H | $C_6H_5C(O)O$ | OH |
| I-a' | β-D-isomer | H | OH | H | OH |
| I-b' | β-D-isomer | $CH_3$ | OH | H | OH |
| I-c' | β-D-isomer | $CH_3CH_2$ | OH | H | OH |
| I-d' | β-D-isomer | $CH_3CH_2CH$ | OH | H | OH |
| I-e' | β-D-isomer | $BrCH=CH$ | OH | H | OH |
| I-f' | β-D-isomer | $C_6H_5CH_2$ | OH | H | OH |
| I-g' | β-D-isomer | H | $C_6H_5C(O)O$ | H | OH |
| I-h' | β-D-isomer | $CH_3$ | $C_6H_5C(O)O$ | H | OH |
| I-I' | β-D-isomer | $CH_3CH_2$ | $C_6H_5C(O)O$ | H | OH |
| I-j' | β-D-isomer | $CH_3CH_2CH$ | $C_6H_5C(O)O$ | H | OH |
| I-k' | β-D-isomer | $BrCH=CH$ | $C_6H_5C(O)O$ | H | OH |
| I-l' | β-D-isomer | $C_6H_5CH_2$ | $C_6H_5C(O)O$ | H | OH |
| I-m' | β-D-isomer | $F-C_6H_5CH_2$ | OH | H | OH |
| I-n' | β-D-isomer | $NO_2-C_6H_5CH_2$ | OH | H | OH |
| I-o' | β-D-isomer | $NH_2-C_6H_5CH_2$ | OH | H | OH |
| I-p' | β-D-isomer | $Cl-C_6H_5CH_2$ | OH | H | OH |
| I-q' | β-D-isomer | Alkyl-$C_6H_5CH_2$ | OH | H | OH |
| I-r' | β-D-isomer | Methoxy-$C_6H_5CH_2$ | OH | H | OH |
| I-s' | β-D-isomer | Thiol-$C_6H_5CH_2$ | OH | H | OH |
| I-t' | β-D-isomer | $F-C_6H_5CH_2$ | $C_6H_5C(O)O$ | H | OH |
| I-u' | β-D-isomer | $NO_2-C_6H_5CH_2$ | $C_6H_5C(O)O$ | H | OH |
| I-v' | β-D-isomer | $NH_2-C_6H_5CH_2$ | $C_6H_5C(O)O$ | H | OH |
| I-w' | β-D-isomer | $Cl-C_6H_5CH_2$ | $C_6H_5C(O)O$ | H | OH |
| I-x' | β-D-isomer | Alkyl-$C_6H_5CH_2$ | $C_6H_5C(O)O$ | H | OH |
| I-y' | β-D-isomer | Methoxy-$C_6H_5CH_2$ | $C_6H_5C(O)O$ | H | OH |
| I-z' | β-D-isomer | Thiol-$C_6H_5CH_2$ | $C_6H_5C(O)O$ | H | OH |

As mentioned above, the compounds in Table I are illustrative but not limiting. For example, $R^4$ can be not only hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O and other combinations of the structural elements such as described herein, as well as other streochemical orientations, are also possible.

In certain embodiments, acyl derivatives of the 2,2'-anhydropyrimidines of formula (I) are of interest. Thus, compounds of formula (I) include those in which $R^1$, $R^2$, $R^3$ and $R^4$ are as defined above, wherein at least one of $R^2$, $R^3$ and $R^4$ is an acyl derivative. By "acyl derivative" is intended a derivative of a 2,2'-anyhydropyrimidine of formula (I) in which at least one of $R^2$, $R^3$ and $R^4$ is a substantially nontoxic organic acyl substituent obtainable from a carboxylic acid that is attached to a hydroxyl group on the ribose or pyrimidine ring of formula (I) through an ester linkage.

Acyl derivatives of a 2,2'-anyhydropyrimidine compound of formula (I) include those in which $R^1$ is as defined above, and each $R^2$, $R^3$ and $R^4$ is independently hydrogen, hydroxyl or an acyl radical, with the proviso that at least one of $R^2$, $R^3$ and $R^4$ is not hydrogen. In another embodiment, the acyl derivative of a 2,2'-anyhydropyrimidine is a compound of formula (I) in which $R^1$ and $R^2$ are as defined above, with the proviso that $R^2$ is other than hydrogen, and each $R^3$ and $R^4$ is independently hydroxyl or an acyl radical. In one embodiment, the acyl derivative of a 2,2'-anyhydropyrimidine is a compound of formula (I) in which $R^1$ is as defined above, $R^2$ is hydrogen, and each $R^3$ and $R^4$ is independently hydroxyl or an acyl radical. Of particular interest, is an acyl derivative of a 2,2'-anyhydropyrimidine compound of formula (I), wherein $R^1$ is methyl, $R^2$ is hydrogen, and each $R^3$ and $R^4$ is independently hydroxyl or an acyl radical. Also of interest is an acyl derivative of a 2,2'-anyhydropyrimidine compound of formula (I), wherein $R^1$ is methyl, $R^2$ is hydrogen, and each $R^3$ and $R^4$ is an acyl radical.

In general, the ester linkage(s) of an acyl derivative of formula (I) are cleavable under physiological conditions, either in vitro, such as in a cell-based system, and/or in vivo, such as through metabolism in a body. Thus, in certain embodiments, the acyl radical is a radical of a metabolite. Such acyl substituents include, but are not limited to, those derived from acetic acid, fatty acids, amino acids, lipoic acid, glycolic acid, lactic acid, enolpyruvic acid, pyruvic acid, orotic acid, acetoacetic acid, beta-hydroxybutyric acid, creatinic acid, succinic acid, fumaric acid, adipic acid, benzoic acid and p-aminobenzoic acid. Particular acyl substituents of interest are compounds which are normally present in the body, either as dietary constituents or as intermediary metabolites, and which are essentially nontoxic when cleaved from the 2,2'-anyhydropyrimidine compound of interest in vivo.

Of particular interest are compositions comprising a 3'-O-acyl-2,2'-anhydropyrimidine or derivative thereof. For example, acyl derivatives of interest are those that include a 2,2'-anyhydropyrimidine compound of formula (I), where each $R^1$, $R^2$ and $R^3$ is independently selected from selected from hydrogen, hydroxyl, sulfyhydryl, amino, hydroxymethyl, methoxy, halogen, pseudohalogen, and a substituted or unsubstituted lower hydrocarbon containing 1 to 20 carbons, such as a lower hydrocarbon selected from alkyl, alkenyl, alkanoyl, aryl, aroyl, aralkyl and alkylamino, and esters thereof, and where $R^4$ is an O-acyl radical.

In certain embodiments, the acyl derivatives include a 2,2'-anyhydropyrimidine compound of formula (I), where $R^4$ is an O-acyl radical, and where the O-acyl radical comprises 1 to 10 carbon atoms, such as an O-acyl radical selected from aroyloxy, aralkoyloxy, heteroaroyloxy, and cycloalkoyloxy.

Accordingly, acyl derivatives of a 2,2'-anyhydropyrimidine compound of for a (I) include 3'-O-acyl-2,2'-anyhdropyrimidines, 5'-O-acyl-2,2'-anyhydropyrimidines, 3',5'-O-acyl-2,2'-anyhydropyrimidines, and derivatives thereof. For example, 3'-O-acyl-2,2'-anyhydropyrimidines or derivatives thereof include 3'-O-aroyl-2,2'-anyhydropyrimidines, such as a 3'-O-aroyl-2,2'-anyhydrouridine or derivative thereof. An example of particular interest is 3'-O-benzoyl-2,2'-anyhdrouridine or derivative thereof, such as 3'-O-benzoyl-2,2'-anhydro-5-methyluridine. Also of interest is a compound in which the 3'-O-benzoyl-2,2'-anhydro-5-methyluridine is the stereoisomer 3-O-benzoyl-2,2'-anhydro-1-(β-D-arabinofuranosyl)-5-methyluracil.

In some embodiments, acyl derivatives of a 2,2'-anyhydropyrimidine compound of formula (I) include those where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzyloxybenzyl, or acyl radical, and where each $R^3$ and $R^4$ is independently hydroxyl or an acyl radical. These include the compounds: 3'-O-benzoyl-2,2'-anhydrouridine; 3-O-benzoyl-2,2'-anhydro-5-fluorouridine; 3-O-benzoyl-2,2'-anhydro-5-trifluoromethyluridine; 3'-O-benzoyl-2,2'-anhydro-5-methyluridine; 3'-O-benzoyl-2,2'-anhydro-5-ethyluridine; 3'-O-benzoyl-2,2'-anhydro-5-propyluridine; 3'-O-benzoyl-2,2'-anhydro-5-isopropyluridine; 3'-O-benzoyl-2,2'-O-anhydro-5-isobutyluridine; 3'-O-benzoyl-2,2'-anhydro-5-methylacyluridine; 3'-O-benzoyl-2,2'-anhydro-5-propylacyluridine; 3'-O-benzoyl-2,2'-anhydro-5-(2-bromovinyl)-uridine; 3'-O-benzoyl-2,2'-anhydro-5-phenylluridine; 3'-O-benzoyl-2,2'-anhydro-5-benzyluridine; 3'-O-benzoyl-2,2'-anhydro-5-benzyoluridine; and 3'-O-benzoyl-2,2'-anhydro-5-(benzyloxybenzyl)-uridine; 5'-O-benzoyl-2,2'-anhydrouridine; 5'-O-benzoyl-2,2'-anhydro-5-fluorouridine: 5'-O-benzoyl-2,2'-anhydro-5-trifluoromethyluridine; 5'-O-benzoyl-2,2'-anhydro-5-methyluridine; 5'-O-benzoyl-2,2'-anhydro-5-ethyluridine; 5'-O-benzoyl-2,2'-anhydro-5-propyluridine: 5'-O-benzoyl-2,2'-anhydro-5-isopropyluridine; 5'-O-benzoyl-2,2'-O-anhydro-5-isobutyluridine; 5'-O-benzoyl-2,2'-anhydro-5-methylacyluridine; 5'-O-benzoyl-2,2'-anhydro-5-propylacyluridine; 5'-O-benzoyl-2,2'-anhydro-5-(2-bromovinyl)-uridine; 5'-O-benzoyl-2,2'-anhydro-5-phenylluridine; 5'-O-benzoyl-2,2'-anhydro-5-benzyluridine; 5'-O-benzoyi-2,2'-anhydro-5-benzyoluridine; and 5'-O-benzoyl-2,2'-anhydro-5-(benzyloxybenzyl)-uridine; 3',5'-O-benzoyl-2,2'-anhydrouridine; 3',5'-O-benzoyl-2,2'-anhydro-5-fluorouridine; 3',5'-O-benzoyl-2,2'-anhydro-5-trifluoromethyluridine; 3',5'-O-benzoyl-2,2'-anhydro-5-methyluridine; 3', 5'-O-benzoyl-2,2'-anhydro-5-ethyluridine; 3', 5'-O-benzoyl-2,2'-anhydro-5-propyluridine; 3',5'-O-benzoyl-2,2'-anhydro-5-isopropyluridine; 3',5'-O-benzoyl-2,2'-O-anhydro-5-isobutyluridine; 3',5'-O-benzoyl-2,2'-anhydro-5-methylacyluridine; 3',5'-O-benzoyl-2,2'-anhydro-5-propylacyluridine; 3',5'-O-benzoyl-2,2'-anhydro-5-(2-bromovinyl)-uridine; 3',5'-O-benzoyl-2,2'-anhydro-5-phenylluridine; 3',5'-O-benzoyl-2,2'-anhydro-5-benzyluridine; 3',5'-O-benzoyl-2,2'-anhydro-5-benzyoluridine; and 3',5'-O-benzoyl-2,2'-anhydro-5-(benzyloxybenzyl)-uridine; or the pharmaceutically acceptable salts, solvates, hydrates, and prodrug forms thereof, and stereoisomers thereof.

Of specific interest is 3'-O-benzoyl-2,2'-anhydro-5-methyluridine, 5'-O-benzoyl-2,2'-anhydro-5-methyluridine, and 3',5'-O-benzoyl-2,2'-anhydro-5-methyluridine, or the pharmaceutically acceptable salts, solvates, hydrates, and prodrug forms thereof, and stereoisomers thereof. Of specific interest are the β-D-arabinoturanasyl isomers of these compounds, or the pharmaceutically acceptable salts, solvates, hydrates, and prodrug forms thereof.

In another embodiment, compounds according to formula (I) of specific interest are those where $R^1$ and $R^4$ are as defined above, and $R^2$ and/or $R^3$ is a cyclic hydrocarbyl. By "cyclic hydrocarbyl" is intended a hydrocarbon-based ring structure having from 3 to about 10 carbon atoms and having a single cyclic ring or multiple condensed rings that may be substituted. Cyclic hydrocarbyls of interest are selected from aryl, aralkyl, aryloxy, aroyl, aroyloxy, heteroaryl, heteroaryloxy, heteroaroyloxy, cylcoalkyl, cycloalkyloxy and cycloalkoyloxy. Thus, cyclic hydrocarbyls of special interest are O-linked to the ribose or pyrimidine ring of formula (I). Compounds where $R^2$ and/or $R^3$ is a cyclic hydrocarbyl exhibit improved activity on a molar basis, or improved specificity with respect to not interfering with cancer therapy efficacy.

Accordingly, certain compounds of the invention comprise a 5'-O-(cyclic hydrocarbyl)-2,2'-anhydropyrimidine or derivative thereof. This embodiment includes 5'-O-(cyclic hydrocarbyl)-2,2'-anhydro-5($R^5$)-uridine or derivatives thereof, where $R^5$ is $R^1$ (eg, $R^5$=$R^1$ where "5($R^5$)" refers to, and is the same as, $R^1$ of formula (I)).

A compound of interest is 5'-O-aryl-2,2'-anhydropyrimidine or derivative thereof, of which various 2,2'-anhydrouridine derivatives are of included. This includes compounds where the 5'-O-aryl-2,2'-anhydropyrimidine is a 5'-O-aroyl-2,2'-anhydropyrimidine, such as: 5'-O-benzoyl-2,2'-anyhydropyrimidine; 5'-O-chlorobenzyl-2,2'-anhydropyrimidine;

5'-O-nitrobenzyl-2,2'-anhydropyrimidine; 5'-O-hydroxybenzyl-2,2'-anhydropyrimidine, and the like.

In one embodiment, compounds that exhibit improved activity on a molar basis or improved specificity with respect to not interfering with fluorouracil therapy efficacy are the 5'-O-aryl-2,2'-anhydrouridines, 5'-O-aroyl-2,2'-anhydrouridines, and derivatives thereof, such as 5'-O-aryl-2,2'-anhydro-5($R^4$)-uridine, 5'-O-aroyl-2,2'-anhydro-5($R^4$)-uridine, and their derivatives. Examples include 5'-O-aryl-2,2'-anhydro-5-methyl-uridine; 5'-O-aryl-2,2'-anhydro-5-ethyl-uridine; 5'-O-aryl-2,2'-anhydro-5-propyl-uridine; 5'-O-aryl-2,2'-anhydro-5-benzyl-uridine; and 5'-O-aryl-2,2'-anhydro-5-(2-bromovinyl)-uridine; and derivatives thereof. Examples also include 5-O-aroyl-2,2'-anhydro-5-methyl-uridine; 6-O-aroyl-2,2'-anhydro-5-ethyl-uridine; 5-O-aroyl-2,2'-anhydro-5-propyl-uridine; 5-O-aroyl-2,2'-anhydro-5-benzyluridine; and 5-O-aroyl-2,2'-anhydro-5-(2-bromovinyl)-uridine; and derivatives thereof. Compounds of specific interest include 5'-O-benzoyl-2,2'-anhydro-5($R^4$)-uridines, such as 5'-O-benzoyl-2,2'-anhydro-5-methyl-uridine; 5'-O-benzoyl-2,2'-anhydro-5-ethyl-uridine; 5'-O-benzoyl-2,2'-anhydro-5-propyl-uridine; 5'-O-benzoyl-2,2'-anhydro-5-benzykuridine, and 5'-O-benzoyl-2,2'-anhydro-5-(2-bromovinyl)-uridine.

Stereoisomers of interest include the 5'-O-(cyclic hydrocarbyl)-2,2'-anhydropyrimidines which are the β-D-isomers. Examples include, but are not limited to: 5'-O-benzoyl-2,2'-anhydro-1-(β-D-arabinofuranosyl)uracil; 5'-O-benzoyl-2,2'-anhydro-1-(β-D-arabinofuranosyl)-5-fluorouracil; benzoyl-2,2'-anhydro-1-(β-D-arabinofuranosyl)-5-trifluoromethyluracil; 5'-O-benzoyl-2,2'-anhydro-1-(β-D-arabinofuranosyl)-5-methyluracil; 5'-O-benzoyl-2,2'-anhydro-1-(β-D-arabinofuranosyl)-5-ethyluracil; 5'-O-benzoyl-2,2'-anhydro-1-(β-D-arabinofuranosyl)-5-n-propyluracil; 5'-O-benzoyl-2,2'-anhydro-1-(β-D-arabinofuranosyl)-5-isopropyluracil, 5'-O-benzoyl-2,2'-anhydro-1-(β-D-arabinofuranosyl)-5-isobutyluracil; 5'-O-benzoyl-2,2'-anhydro-1-(β-D-arabinafuranosyl)-5-methyacyluracil; 5'-O-benzoyl-2,2'-anhydro-1-(β-D-arabinofuranosyl)-5-propylacyluracil; 5'-O-benzoyl-2,2'-anhydro-1-(β-D-arabinofuranosyl)-5-(2-bromovinyl)uracil; 5'-O-benzoyl-2,2'-anhydro-1-(β-D-arabinofuranosyl)-5-phenyluracil; 5'-O-benzoyl-2,2'-anhydro-1-(β-D-arabinofuranosyl)-5-benzyluracil; 5'-O-benzoyl-2,2'-anhydro-1-(β-D-arabinofuranosyl)-5-benzyoluracil; and 5'-O-benzoyl-2,2'-anhydro-1-(β-D-arabinofuranosyl)-5-(3-benzyoxybenzyl)uracil.

As noted above, also of interest are analogues/derivatives of the above compounds, where such analogs/derivatives reduce cancer therapy toxicity, such that cancer therapy toxicity is reduced when the compounds are administered in conjunction with a cancer therapy according to the subject invention. As also indicated above, an effective amount of cancer therapy toxicity-reducing adjuvant is employed in the subject methods.

The 2,2'-anhydropyrimidine and derivatives thereof described above are commercially available or can be conventionally prepared by techniques known to one of skill in the art. For example, representative patents describing various 2,2'-anhydropyrimidine and derivatives, including intermediates and precursors, analysis, as well as the synthesis/preparation thereof, include U.S. Pat. Nos. 3,975,367; 4,145,531; 4,230,698; 4,247,544; 4,544,740; 4,604,382; 4,613,604; 4,681,933; 4,841,039; 4,916,122; 4,987,224; 5,008,384; 5,077,280; 5,084,445; 5,141,943; 5,190,926; 5,212,293; 5,278,167; 5,384,396; 5,455,339; 5,476,855; 5,596,093; 5,610,292; 5,721,241; 5,723,449; 5,739,314; 5,760,202; 5,889,013; 5,861,493; 6,060,592; 6,090,932; 6,222,025; 6,369,040; 6,642,367; 6,670,461; 6,867,290; and 7,176,295; the disclosures of which are herein incorporated by reference.

UR and sources thereof include, but are not limited to: meat products, such as fish, pig and cow liver and pancreas, and the like; fungi related products, such as brewer's yeast, beer, mushrooms, and the like; vegetable products, such as sugarcane, tomatoes, oats, algae, broccoli and the like; salts, such as UR phosphates, acylated UR, and the like. UR and sources thereof which may be employed in embodiments of the invention include, but are not limited to, those described in U.S. Pat. Nos. 9,579,337; 6,316,426; and 5,470,838; the disclosures of which compounds are incorporated herein by reference.

UR precursors and sources thereof include, but are not limited to: prodrugs of UR, such as triphenyluridine, orotic acid and the like; prodrugs of uridine 5'-monophosphate, such as mono- and di-alkyl esters, acyloxyalkyl esters, alkoxycarbonylmethyl esters, substituted ethyl and propyl esters, amidomethyl esters, benzyl esters phenyl esters, phosphonamidates, cyclophosphate esters and the like; UR prodrugs containing mono-, di- or tri-esters of UR, such as mono-, di-, and triacetyl UR and the like; UR prodrugs containing mono, di- or tri-phosphates of UR, such as UR monophosphate, UR diphosphate, UR triphosphate and the like; UR hornodimers and their esters, such as U-P-U and the like; heterodimers of dideoxynucleoside compounds and UR or UPase inhibitors, such as AZT-P-U and AZT-P-BAU; etc. Uridine precursors and sources thereof which may be employed in embodiments of the invention include, but are not limited to, those described in U.S. Pat. Nos. 5,723,449 and 7,737,128; the disclosures of which compounds are incorporated herein by reference.

Uridine phosphorylase (UPase) inhibitors include, but are not limited to: benzylacyclouridine, benzyloxyacylouridine, aminomethyl-benzylacylouridine, aminomethyl-benzyloxybenzylacyclouridine, hydroxymethyl-benzylacyclouridine, hydroxymethyl-benzyloxybenzyl acyclouridine, and the like; derivatives of 5-benzylbarbiturate, such as 5-benzyloxybenzyl barbiturate; 5-benzyloxybenzyl-1-(1-hydroxy-2-ethoxy)methyl) barbiturate; 5-benzyloxybenzylacetyl-1-(1-hydroxy-2-ethoxy) methyl) barbiturate; 5-benzyloxybenzyl-1-(1,3-dihydroxy 2-propoxy)methyl barbiturate; 5-benzyloxybenzyl-1-1-hydroxy, 3-amino-2-propoxy) methyl) barbiturate; 5-benzyloxybenzyl-1-(2-(3-carboxypropionyloxy)ethoxy) methyl) barbiturate; 5-benzyl-1-(1-hydroxy-2-ethoxy) methyl) barbiturate; 5-methoxybenzylacetyl barbiturate; 5-benzyl-1-(1,3-dihydroxy-2-propoxy)methyl) barbiturate; 5-benzyl-1-(1-hydroxy, 3-amino-2-propoxy)methyl) barbiturate; and 5-benzyl-1-(2-(3-carboxypropionyloxy)ethoxy) methyl) barbiturate, and the like. Upase inhibitors which may be employed in embodiments of the invention include, but are not limited to, those described in U.S. Pat. Nos. 5,723,449; 5,141,943; 5,077,280; and 4,613,604; the disclosures of which compounds are incorporated herein by reference.

UR secretion inhibiting compounds include, but are not limited to: drugs, such as dilazep, hexobendine. UR secretion inhibiting compounds which may be employed in embodiments of the invention include, but are not limited to, those described in U.S. Pat. Nos. 6,989,376 and 5,567,689; the disclosures of which compounds are incorporated herein by reference.

UR renal transport competitors include, but are not limited to drugs, such as L-uridine, dideoxyuridine, D-2',3'-dideoxyuridine. UR renal transport competitors which may be employed in embodiments of the invention include, but are not limited to, those described in U.S. Pat. Nos. 6,989, 376; 5,723,449 and 5,567,689; the disclosures of which compounds are incorporated herein by reference.

Subjects that are treated according to methods of the invention may be subjects suffering a pulmonary condition, such as a severe pulmonary condition, e.g., IPF, ARDS, etc. Treatment according to the disclosed methods can begin prophylactically for subjects at risk for lung disease or post diagnosis of a serious lung condition. Treatment can be carried out at intervals determined to be appropriate by those of skill in the art. For example, the administration can be carried out 1, 2, 3, 4 or more times/day. Ideally, treatment is expected to be qd chronically. Treatment can also be started before or at or near the same time as a drug associated with serious lung conditions.

Formulations

Also provided are pharmaceutical compositions containing the UR plasma level modulator employed in the subject methods. Accordingly, the plasma UR level modulator may be present in pharmaceutical compositions, e.g., in the form of a pharmaceutically acceptable salt, and can be formulated for oral, topical or parenteral administration for use in the subject methods, as described above. In certain embodiments, e.g., where the UR elevation agent and UR, UR pro-drug or an UR mimetic are used together perhaps in a common formulation.

By way of illustration, UR plasma level modulator and if needed the UR pro-drug or UR mimetic (separately or in combination) can be admixed with conventional pharmaceutically acceptable carriers and excipients (ie, vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s), In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an anti-oxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"), Such compositions include, for example, a backing, active compound reservoir, a control membrane, liner and contact adhesive. Such transdermal patches may be used to provide continuous or discontinuous infusion of the compounds of the present invention in controlled amounts, The construction and use of transdermal patches for the delivery of pharmaceutical agents is well known in the art. See, eg, U.S. Pat. No. 5,023,252, herein incorporated by reference in its entirety. Such patches may be constructed for continuous, pulsatile, or on demand delivery of pharmaceutical agents.

In certain embodiments of interest, the cancer therapy toxicity-reducing adjuvant and UR plasma level modulator are administered as a single pharmaceutical formulation, that, in addition to including an effective amount of the cancer therapy toxicity-reducing adjuvant and UR plasma level modulator, includes other suitable compounds and carriers, and may also be used in combination with other active agents. The present invention, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present invention may further contain other active agents that are well known in the art.

One skilled in the art will appreciate that a variety of suitable methods of administering a formulation of the present invention to a subject or host, eg, patient, in need thereof, are available, and, although more than one route can be used to administer a particular formulation, a particular route can provide a more immediate and more effective reaction than another route. Pharmaceutically acceptable excipients are also well-known to those who are skilled in the art and are readily available, The choice of excipient will be determined in part by the particular compound, as well as by the particular method used to administer the composition. Accordingly, there are a wide variety of suitable formulations of the pharmaceutical composition of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, and other such carriers that are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

The dose administered to an animal, particularly a human, in the context of the present invention should be sufficient to cause a prophylactic or therapeutic response in the animal over a reasonable time frame. One skilled in the art will recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Suitable doses and dosage regimens can be determined by comparisons to anticancer or immunosuppressive agents that are known to cause the desired growth inhibitory or immunosuppressive response.

Optionally, the pharmaceutical composition may contain other pharmaceutically acceptable components, such as buffers, surfactants, antioxidants, viscosity modifying agents, preservatives and the like. Each of these components is well-known in the art. For example, see U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous solution of cyclodextrin also contains dextrose, e.g., about 5% dextrose.

Utility

The subject methods find use in the treatment of hepatic diseases that feature fibrosis, or the accumulation of extracellular matrix molecules that make up scar tissue as the toxic endpoint as well as other diseases such as, inter alia, pulmonary fibrosis, renal fibrosis, systemic sclerosis (SSc), sclerodermatous graft vs. host disease, radiation-induced fibrosis and cardiac fibrosis. Several eye conditions such as ARMD, DR, ROP, and neovascular glaucoma also feature fibrosis as an endpoint. In aggregate, mitigating fibrosis represent a huge unmet clinical need.

By treatment, is meant that at least an amelioration of the symptoms associated with the condition afflicting the host is achieved, where amelioration is used in a broad sense to refer to at least a reduction in the magnitude of a parameter, e.g., a symptom associated with the condition being treated or an side effect resulting from administration of a drug. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

A variety of subjects are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects will be humans.

In certain embodiments, the subjects will be subjects that have been diagnosed for and are, therefore, in need of administration of the active agent. In certain embodiments, the methods may include diagnosing the subject for the presence of the disease condition to be treated by administration of the active agent. In certain embodiments, the methods may include diagnosing the subject for risk of a disease condition (e.g., fibrosis) whose downstream severity could be modulated or entirely prevented by administration of the active agent.

The dose administered to an animal, particularly a human, in the context of the present invention should be sufficient to affect a prophylactic or therapeutic response in the animal over a reasonable time frame. One skilled in the art will recognize that dosage will depend on a variety of factors including the strength of the particular compound employed and the dosing regimen used, the condition of the animal, and the body weight of the animal, as well as the severity of the illness and the stage of the disease. The size of the dose will also be determined by the existence, nature, and extent of any adverse side-effects that might accompany the administration of a particular compound.

Kits & Systems

Also provided are kits and systems that find use in practicing the subject methods, eg, as described above. For example, kits and systems for practicing the subject methods may include one or more pharmaceutical formulations, which include the UR plasma level modulator and perhaps UR, a UR prodrug, or a UR mimetic. As such, in certain embodiments the kits may include a single pharmaceutical composition, present as one or more unit dosages, where the composition includes both a plasma UR level modulator and perhaps UR, a UR prodrug, or a UR mimetic. In yet other embodiments, the kits may include two or more separate pharmaceutical compositions, each containing the plasma UR level modulator and perhaps UR, a UR prodrug, or a UR mimetic.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits. For example, a kit according to one embodiment includes as a first component (a) instructions for using a plasma UR level modulator, and as a second component (b) a pharmaceutical composition comprising a uridine, an UR prodrug, or an UR mimetic.

Kits of specific interest are those that include a 2,2'-anhydropyrimidine pharmaceutical composition of the invention and suitable for practicing the subject methods of the invention, such as for mitigating serious pulmonary disease.

The term "system" as employed herein refers to a collection of a plasma UR level modulator, and perhaps UR, an UR prodrug or an UR mimetic present in a single or disparate composition, that are brought together for the purpose of practicing the subject methods. For example, separately obtained plasma UR level modulator active agent and perhaps a UR, UR prodrug or UR mimetic dosage forms brought together and co-administered to a subject, according to the present invention, are a system according to the present invention.

The following examples further illustrate the present invention but should not be construed in any way as limiting its scope.

EXAMPLES

FIG. 1. Figure provides a regression analysis of plasma UR concentration versus plasma Compound 1 concentrations determined following continuous infusion of various amounts of Compound 1 (TK-112690) to mice. R2 for the line is 0.95, and the slope and intercept values for the line are 0.010 and 0.051, respectively. Compound 1 is seen to elevate plasma UR in a linear fashion.

Because UR is cleared so rapidly, elimination $t_{1/2}$ only a few minutes, (Deng Y, Wang Z V, Gordillo R, An Y, Zhang C, Liang Q, Yoshino J, Cautivo K M, De Brabander J, Elmquist J K, Horton J D, Hill J A, Klein S, Scherer P E, An adipo-biliary-uridine axis that regulates energy homeostasis, Science 2017, 17; 355(6330) and the elimination $t_{1/2}$ of Compound 1 in mice is only 1-2 hours, it is very challenging to measure UR concentrations elevations post discrete doses of Compound I, such as used for ip dosing. For this reason continuous infusion of compound I (authentic TK-112690, Batch TCY90108) to BDF-1 ♂ mice were administered via a sc implanted osmotic pumps and the UR plasma concentration measured.

Solutions of Compound I were prepared at a concentration of 500 mg/mL in sterile PBS. Osmotic pumps (ALZET® micro-osmotic pump 2001D and 1003D, Alza Co) were loaded with 200 µL (2001D osmotic pump) and/or 100 µL (1003D osmotic pump) of TK-112690 solution.

BDF-1 male mice (n=6) were treated with a constant-rate infusion of 667, 833 or 3000 mg/kg/day doses of Compound I delivered via subcutaneously implanted osmotic pumps. Animals were anesthetized with 100 mg/kg ketamine prior to pump implantation. Surgical scissors were used to make an approximately 1 cm incision on the dorsal surface near the shoulder blade of animals. A hemostat was used to carve out a subcutaneous tunnel toward the anterior end of animal. Osmotic pumps were placed inside the subcutaneous tunnel. Incision was sealed with wound clips.

Blood collections were performed on animals anesthetized with ketamine (ip 100 mg/kg). Blood samples from animals treated with a constant-rate infusion of TK-112690 were collected at 72 hours for 667 mg/kg/day and 833 mg/kg/day and 24 hours for 3000 mg/kg/day after pump implantation. Whole blood (~0.8 mL) was drawn through the retro-orbital sinus using a heparin coated micro-hematocrit tube and collected into an EDTA microtainer tube. Blood samples were transferred into fresh 1.5 mL microcentrifuge tubes and centrifuged for 10 minutes at 14,000×g using an Eppendorf Minispin Plus stored in a 4° C. refrigerator. Exactly 0.4 mL of plasma was transferred into fresh microcentrifuge tubes containing 2 μL of 10 mM 5-FU and vortexed at highest setting for approximately 5 seconds. The final 50 μM concentration of 5-FU served as an internal standard. Animals were sacrificed by cervical dislocation and properly disposed.

Blood samples from animals treated with a constant-rate infusion of compound I were collected at 72 hours for 667 mg/kg/day and 833 mg/kg/day and 24 hours for 3000 mg/kg/day after pump implantation. Whole blood (~0.8 mL) was drawn through the retro-orbital sinus using a heparin coated micro-hematocrit tube and collected into an EDTA microtainer tube. Blood samples were transferred into fresh 1.5 mL microcentrifuge tubes and centrifuged for 10 minutes at 14,000×g using an Eppendorf Minispin Plus stored in a 4° C. refrigerator. Exactly 0.4 mL of plasma was transferred into fresh microcentrifuge tubes containing 2 μL of 10 mM 5-FU and vortexed at highest setting for approximately 5 seconds. The final 50 μM concentration of 5-FU served as an internal standard. Animals were sacrificed by cervical dislocation and properly disposed.

A solid-phase extraction (SPE) of analytes (UR, Compound I and 5-FU) from plasma was conducted before HPLC analysis. Supelco C8 SPE columns were used for extraction process. All solutions were pushed through SPE columns using positive pressure generated from a Vacuum-Pressure Pump (Barnant Company Model 400-1901). The flow rate through the SPE column was approximately 2 drops per second. Pre-washing of SPE columns was done with a total of 2.4 mL of sterile PBS (room temp; pH=7.4). Exactly 0.6 mL PBS was added to the SPE column four separate times and pushed through the column. Immediately after pre-wash, all 0.4 mL of the plasma sample (with added 5-FU internal standard) was transferred onto the column and pushed through the column. Analytes were disassociated from SPE column by pushing through exactly 0.5 mL of 5 M NaCl (room temp; pH~5). Eluted samples were collected into fresh 1.5 mL micro-centrifuge tubes. Samples were transferred into fresh HPLC vials and analyzed.

HPLC analysis was done at room temperature (RT) using a ThermoFinnigan Spectra System equipped with degasser, pump, autosampler and UV detector. Chromatograms were constructed from a chart recorder equipped with a pen. Analytes were separated using a Phenomenex C18 Reverse-Phase column (250×4.6 mm). Two separate mobile phase gradients were employed for the HPLC analysis: (1) 5% methanol in nano water with 0.1% formic acid (2) 5% methanol in acetonitrile with 0.1% formic acid (flow rate=0.5 mL per minute). HPLC responses for compound and UR were divided by the 5-FU response. Calibration curves were used to convert these ratios into concentrations of Compound 1.

A regression analysis (UR concentration vs. Compound 1 concentration) for data from the study is provided in FIG. 1. Higher concentration of TK-112690 (Compound 1) are seen to be associated with higher levels of UR.

Figure 2:
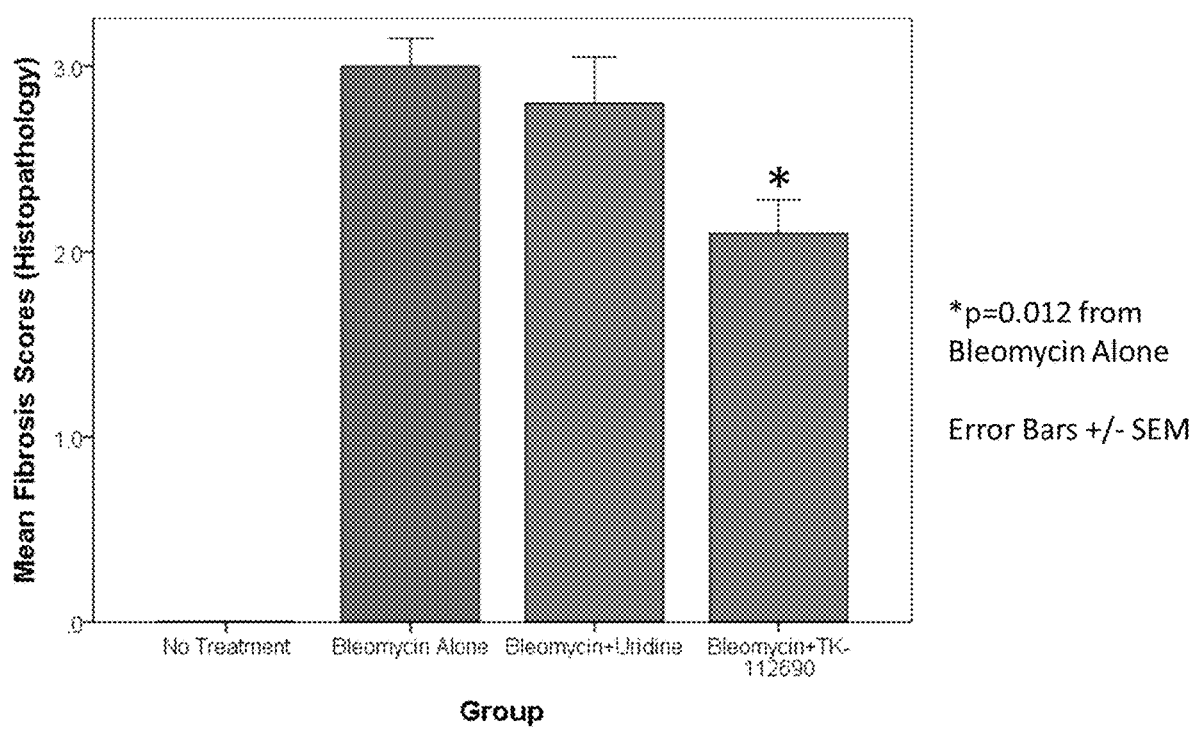
FIG. 2. Figure is a chart providing histology scores for pulmonary tissue from mice all treated with bleomycin (a well characterized lung toxin) and either dosing vehicle, UR or TK-112690. Mice treated with TK-112690 showed a statistically significant 30% less fibrosis than mice treated with the dosing vehicle. Mice treated with UR showed only a 7% decrease in fibrosis compared to the dosing vehicle, and the result was not statistically significant.

FIG. 2. Figure is a chart providing histology scores for pulmonary tissue from mice treated with bleomycin (a well characterized lung toxin) and either dosing vehicle, UR, or TK-112690.

Thirty-three C57BL/6 male mice, 10-14 weeks at study initiation, were acclimatized for least 3 days. The mouse has been selected as is referenced in the literature as a representative species of choice for this experimental animal model. During acclimation and throughout the entire study duration, animals were housed within a limited access rodent facility and kept in groups of a maximum of 4 mice per cage. Mice were housed in polypropylene cages with solid bottoms and wood shavings or corn Cobb as bedding material. Animals were provided ad libitum with a commercial rodent diet and had free access to drinking water that is supplied to each cage via polyethylene bottles. The automatically controlled environmental conditions was set to maintain temperature at 20-26° C. with a relative humidity (RH) of 30-70%, a 12:12 hour light: dark cycle, and 10-15 air changes/hour in the study room. Animals were given a unique animal identification tail mark as a means of identification. This number also appeared on a cage card, which is visible on the front of each cage. The cage card also contains the study and group numbers, route of administration, gender, study director and arrival date.

Animals were randomly assigned to cages on arrival. Animals were assigned to treatment groups prior to treatment initiation. At study termination, surviving animals were weighed prior to euthanasia. Euthanasia was performed via anesthesia overdose and exsanguination.

The table below lists the experimental group(s) comprising the study.

| Group Number | Group Size* | Disease Induction | Treatment | Route | Dose* | Dosing volume* | Dosing Regime |
|---|---|---|---|---|---|---|---|
| 1 | N = 3 | NA | Naive | NA | NA | NA | NA |
| 2 | N = 10 | 75 μl of | Disease only | NA | NA | NA | NA |
| 3 | N = 10 | bleomycin administered | Uridine | IP | 60 mg/kg | 10 ml/kg | BID Days 7 through 20 |
| 4 | N = 10 | via OA on day 0 | TK-112690 | IP | 60 mg/kg | 10 ml/kg | BID Days 7 through 20 |

*Dosing volume is based on average body weight per group, typically approx. 20 g/mouse.

Disease Induction. 75 uL of Bleomycin (section 4.5.) was administered on day 0 via oropharyngeal aspiration (O.A.). The mice were anesthetized via isoflurane/oxygen and suspended by their cranial incisors on a thin wire from an angled stand. The tongue was be gently held from the mouth using blunt forceps to visualize the base of the tongue and the pharynx. Bleomycin/saline suspension was pipetted onto posterior pharynx. Nostrils will be held gently closed. Respiration was monitored to ensure the suspension is fully aspirated.

Treatment. Groups 3 and 4 were treated via intraperitoneal (IP) injection at a dosing volume of 10 ml/kg twice daily, 6-8 hours between doses, from days 7 through 20.

Observations and Examinations. Clinical signs, humane endpoints, and palliative care: Changes in skin, fur, eyes, mucus membranes, occurrence of secretions and excretions, autonomic activity, gait, posture, and response to handling, Bizarre behavior, tremors, convulsions, sleep and coma. Laboring breathing and adventitious lung sounds.

The bleomycin administration induced a severe pulmonary inflammation resulting in lethargy, dehydration, and death of diseased animals. Animals in all diseased groups were given fresh diet gel daily beginning on Day 7 and through the remainder of the study. Body weight measurements were performed 3× weekly starting on Day 0 and throughout the rest of the study.

Termination: BALF and tissue collection. Animals were euthanized via isoflurane overdose, Following euthanasia an angiocatheter was inserted into the trachea. 1 ml of PBS was instilled into the lungs and allowed to flow back out into the syringe twice. The resulting BALF was centrifuged at 500×g for 5 mins and the non-cellular portion of the BALF was stored at −80° C. for potential subsequent analyses.

Histology. Following BALF collection, lungs were inflated and fixed with formalin for histological analysis. Analysis included Masson's Trichrome stain for presence of collagen. Disease severity and collagen levels were assessed by the Ashcroft fibrosis grading system.

The resulting data were analyzed by SPSS, version 20. The mice treated with TK-112690 showed a statistically significant 30% less fibrosis than mice treated with the dosing vehicle. Mice treated with UR showed only a 7% decrease in fibrosis compared to the dosing vehicle, and the result was not statistically significant.

Figure 3:
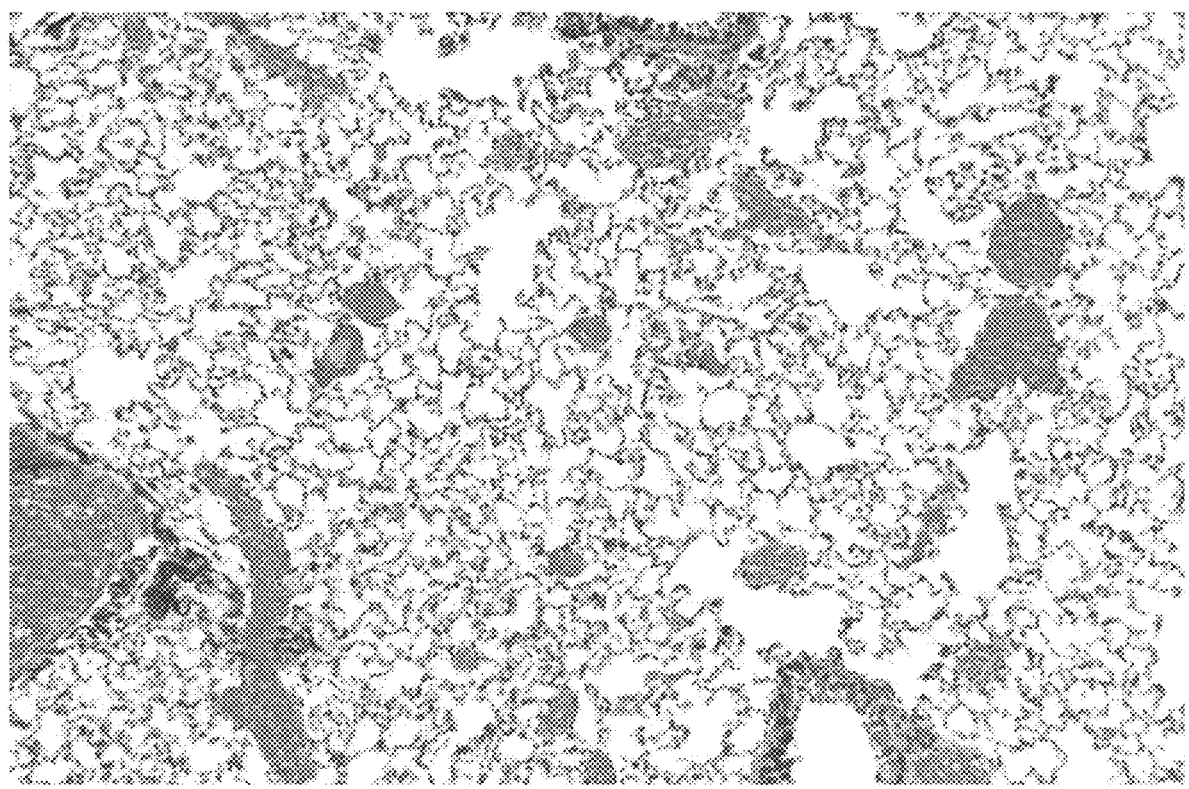
FIG. 3A-D. Figure provides representative lung sections from each of the four experimental groups from the bleomycin/pulmonary fibrosis study summarized in FIG. 2. The lung sections were stained by Masson's trichrome.

FIG. 3. Figure provides representative H&E images of lung sections from each experimental group for the bleomycinipulmonary fibrosis study shown in FIG. 2. Total lung was weighed, formalin fixed and stained. Analysis used Masson's Trichrome stain to detect presence of collagen. The histopathologic measurement of fibrosis was performed by an experienced histopathologist.

Figure 4:
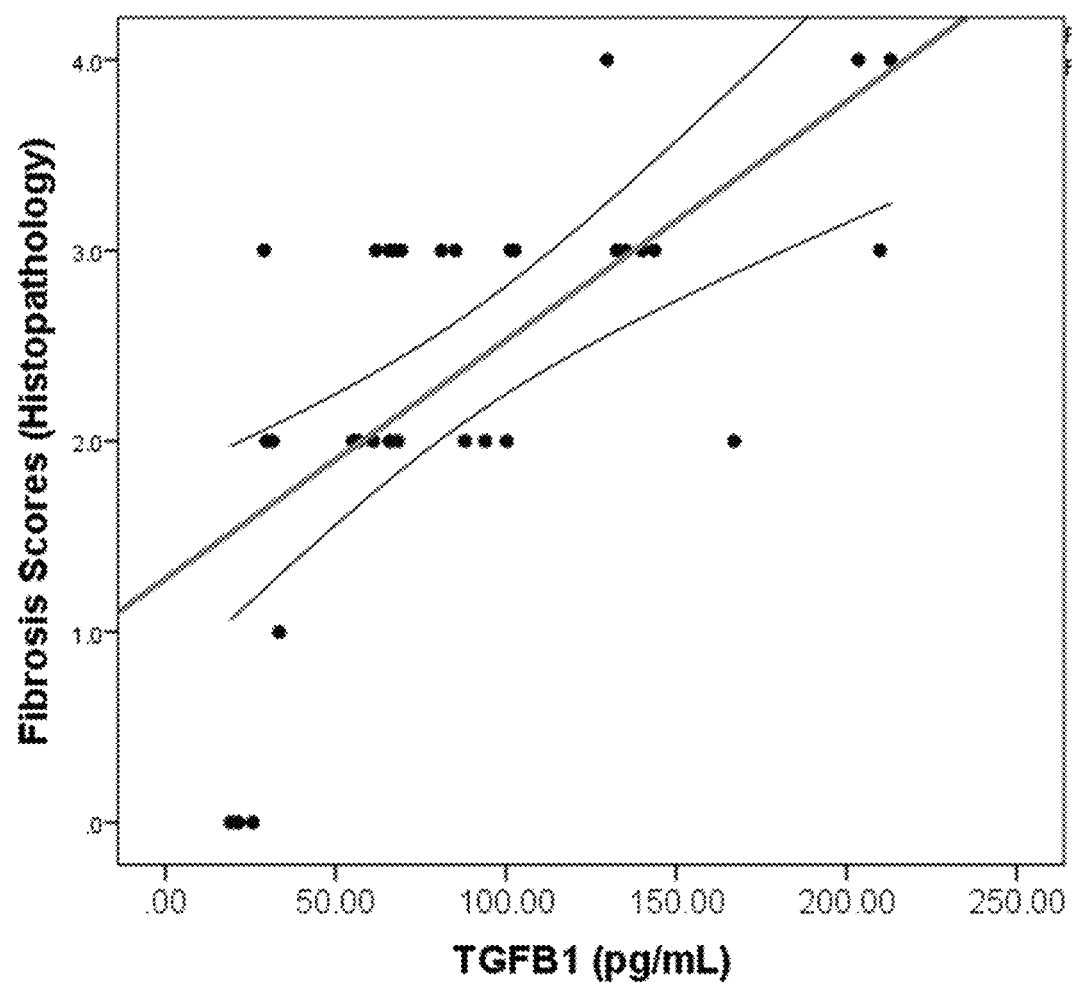
FIG. 4. Figure provides a correlation between fibrosis scores and TGF-β levels in BAL fluid from the mice participating in the bleomycin/pulmonary fibrosis study whose results are shown in FIG. 2. Although, considerable variability in TGFβ concentrations are observed, a statistically significant correlation between fibrosis scores and TGF-β concentrations are observed.

FIG. 4. Figure provides a chart correlating TGF-β1 concentration in BAL fluid from the mice participating in the bleomycinipulmonary fibrosis study whose results are shown in FIG. 2 and fibrosis scores. Each BAL sample was 60 µl of BALF in 1.5 ml Eppendorf tubes. Prior to analysis the samples were stored at −80° C. The samples were run at a single concentration without any dilutions. Duplicates of each calibration standard were run, so that the CV values could also be evaluated for the panel.

Samples were analyzed using a Luminex® MagPix™ system. Analysis of the raw data was performed using Milliplex™ Analyst software. The Luminex technology used color-code microspheres with fluorescent dyes which were coated with a specific capture antibody. After incubation of the analyte with captured beads, a biotinylated detection secondary antibody is introduced followed by a reporter molecule (Streptavidin-PE conjugate). The analyte concentration was quantified based on the fluorescent reporter signal. The best-fit standard curve was determined by regression analysis using five-parameter logistic curve-fit.

SPSS, version 20, was used to perform the correlation evaluation. The observed correlation coefficient, 0.66, was significant at the 0.01 level (2-tailed). The green line in the plot is the regression line for the data. The curved black lines in the plot are the 95% confidence limits for the regression.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter, All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112(f) or 35 U.S.C. § 112(6) is not invoked.

What is claimed is:

1. A method of treating a pulmonary condition caused by fibrosis, the method comprising: administering to a subject diagnosed with the pulmonary condition or diagnosed to be at risk for the pulmonary condition an effective amount of a 2,2'-anhydropyrimidine or derivative thereof to ameliorate fibrosis to treat the subject for the pulmonary condition.

2. The method according to claim 1, wherein the 2,2'-anhydropyrimidine or derivative thereof is a compound of formula (I):

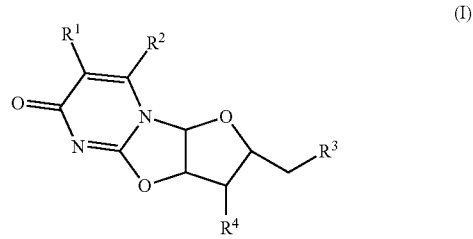

or the pharmaceutically acceptable salts, solvates, hydrates, and prodrug forms thereof, and stereoisomers thereof;

wherein:

each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, carbohydrate, nucleic acid, amino acid, peptide, dye, fluorophore and polypeptide.

3. The method according to claim 2, wherein each $R^1$, $R^2$, $R^3$ and $R^4$ is independently selected from the group consisting of hydrogen, hydroxyl, sulfyhydryl, amino, hydroxymethyl, methoxy, halogen, pseudohalogen, and a substituted or unsubstituted lower hydrocarbon containing 1 to 20 carbons.

4. The method according to claim 3, wherein the lower hydrocarbon is selected from the group consisting of alkyl, alkenyl, alkanoyl, aryl, aroyl, aralkyl and alkylamino, and esters thereof.

5. The method according to claim 2, wherein $R^1$ is hydrogen, fluorine, methyl, ethyl, propyl, benzyl, or 2-bromovinyl; $R^2$ is hydrogen, hydroxyl fluorine, methyl, ethyl, propyl, benzyl, benzoyl, benzoyloxy, or 2-bromovinyl; and each $R^3$ and $R^4$ is independently selected from the group consisting of hydroxyl and benzoyloxy.

6. The method according to claim 5, wherein $R^1$ is hydrogen or methyl; $R^2$ is hydrogen; and each $R^3$ and $R^4$ is independently selected from the group consisting of hydroxyl and benzoyloxy.

7. The method according to claim 1, wherein the 2,2'-anhydropyrimidine or derivative thereof is selected from the group consisting of: 2,2'-anhydro-5-methyluridine; 3'-O-benzoyl-2,2'-anhydrouridine; 3'-O-benzoyl-2,2'-anhydro-5-methyluridine; 5'-O-benzoyl-2,2'-anhydrouridine; and 5'-O-benzoyl-2,2'-anhydro-5-methyluridine.

8. The method according to claim 7, wherein the 2,2'-anhydropyrimidine or derivative thereof is 2,2'-anhydro-5-methyluridine.

9. The method according to claim 7, wherein the 2,2'-anhydropyrimidine or derivative thereof is 3'-O-benzoyl-2,2'-anhydro-5-methyluridine.

10. The method according to claim 7, wherein the 2,2'-anhydropyrimidine or derivative thereof is 5'-O-benzoyl-2,2'-anhydro-5-methyluridine.

11. The method according to claim 1, wherein the 2,2'-anhydropyrimidine or derivative thereof comprises a stereoisomer.

12. The method according to claim 11, wherein the stereoisomer is selected from the group consisting of 2,2'-anhydro-1-(β-D-arabinofuranosyl)-5-methyluracil; 3'-O-benzoyl-2,2'-anhydro-1-(β-D-arabinofuranosyl)-uracil; 3'-O-benzoyl-2,2'-anhydro-1-(β-D-arabinofuranosyl)-5-methyluracil; 5'-O-benzoyl-2,2'-anhydro-1-(β-D-arabinofuranosyl)-uracil; and 5'-O-benzoyl-2,2'-anhydro-1-(β-D-arabinofuranosyl)-5-methyluracil.

13. The method according to claim 1, wherein the 2,2'-anhydropyrimidine or derivative thereof is administered to the subject suffering NAFLD.

14. The method according to claim 1, wherein the 2,2'-anhydropyrimidine or derivative thereof is administered to the subject suffering NASH.

15. The method according to claim 1, wherein the 2,2'-anhydropyrimidine or derivative thereof is administered to the subject suffering a DILI.

16. The method according to claim 11, wherein the 2,2'-anhydropyrimidine or derivativ thereof is administered to the subject likely to suffer a DILI because of planned treatment.

17. A method of treating a pulmonary condition caused by fibrosis, the method comprising:
administering to a subject diagnosed with the pulmonary condition or diagnosed to be at risk fo the pulmonary condition an effective amount of a 2,2'-anhydropyrimidine or derivative thereof in combination with one or more of UR, an UR prodrug and an UR mimetic to ameliorate fibrosis to treat the subject for the pulmonary condition.

18. The method according to claim 17, wherein the 2,2'-anhydropyrimidine or derivative thereof is a compound of formula (I):

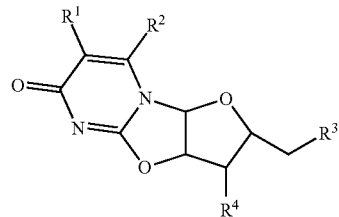

or the pharmaceutically acceptable salts, solvates, hydrates, and prodrug forms thereof, and stereoisomers thereof;

wherein:

each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, carbohydrate, nucleic acid, amino acid, peptide, dye, fluorophore and polypeptide.

19. The method according to claim 18, wherein each $R^1$, $R^2$, $R^3$ and $R^4$ is independently selected from the group consisting of hydrogen, hydroxyl, sulfyhydryl, amino, hydroxymethyl, methoxy, halogen, pseudohalogen, and a substituted or unsubstituted lower hydrocarbon containing 1 to 20 carbons.

20. The method according to claim 19, wherein the lower hydrocarbon is selected from the group consisting of alkyl, alkenyl, alkanoyl, aryl, aroyl, aralkyl and alkylamino, and esters thereof.

* * * * *

UNITED STATES PATENT AND TRADEMARK OFFICE
CERTIFICATE OF CORRECTION

| | | |
|---|---|---|
| PATENT NO. | : 12,194,043 B2 | |
| APPLICATION NO. | : 17/369203 | |
| DATED | : January 14, 2025 | |
| INVENTOR(S) | : William A. Garland et al. | |

It is certified that error appears in the above-identified patent and that said Letters Patent is hereby corrected as shown below:

In the Specification

Please replace "aroups" with -- groups -- (Column 5, Line 23).

Please replace "branched," with -- branched. -- (Column 7, Line 17).

Please replace ""Aminocarbonyi"" with -- "Aminocarbonyl" -- (Column 7, Line 42).

Please replace ""Aminocarbonyiamino"" with -- "Aminocarbonylamino" -- (Column 7, Line 45).

Please replace ""Aminocarbonylonxy"" with -- "Aminocarbonyloxy" -- (Column 7, Line 49).

Please replace "atom," with -- atom. -- (Column 10, Line 47).

Please replace "groups," with -- groups. -- (Column 11, Line 15).

Please replace "hornopiperazinyl," with -- homopiperazinyl, -- (Column 11, Line 27).

Please replace "=NR$^3$," with -- "=NR$^8$, -- (Column 14, Line 52).

Please replace "Thiaketo"" with -- "Thioketo" -- (Column 15, Line 5).

Please replace "133-44)," with -- 133-44). -- (Column 18, Line 3).

Please replace "R'," with -- R$^1$, -- (Column 18, Line 35).

Please replace "pentafluorobenzayl" with -- pentafluorobenzoyl -- (Column 19, Line 10).

Please replace "p-nitrobenzayl" with -- p-nitrobenzoyl -- (Column 20, Line 25).

Signed and Sealed this
Twenty-second Day of April, 2025

Coke Morgan Stewart
*Acting Director of the United States Patent and Trademark Office*

CERTIFICATE OF CORRECTION (continued)
U.S. Pat. No. 12,194,043 B2

Please replace "O-(m-chlorobenzoyl))," with -- O-(m-chlorobenzoyl)), -- (Column 20, Line 41).

Please replace "pentaflourobenzayloxy." with -- pentaflourobenzoyloxy. -- (Column 21, Line 12).

Please replace "rnonoalkylamino," with -- monoalkylamino, -- (Column 21, Line 14).

Please replace "$C_8H_5O$" with -- $C_6H_5O$ -- (Column 22, Line 67).

Please replace "substituent," with -- substituent. -- (Column 23, Line 2).

Please replace "benzayloxy." with -- benzoyloxy. -- (Column 23, Line 35).

Please replace "arabinafuranosyl)-" with -- arabinofuranosyl)- -- (Column 24, Line 39).

Please replace "-5-phenyluracii;" with -- -5-phenyluracil; -- (Column 24, Line 40).

Please replace "-benzoyi-" with -- -benzoyl- -- (Column 24, Line 45).

Please replace "-arabinofuranosyl)-" with -- -arabinofuranosyl)- -- (Column 24, Line 51).

Please replace "arabinafuranosyl)-" with -- arabinofuranosyl)- -- (Column 25, Line 1).

Please replace "for a" with -- formula -- (Column 27, Line 35).

Please replace "fluorouridine:" with -- fluorouridine; -- (Column 28, Line 4).

Please replace "-propyluridine:" with -- -propyluridine; -- (Column 28, Line 7).

Please replace "-benzoyi-" with -- -benzoyl- -- (Column 28, Line 14).

Please replace "β-D-arabinoturanasyl" with -- β-D-arabinofuranosyl -- (Column 28, Line 38).

Please replace "hydrocarbyl)-" with -- hydrocarbyl)- -- (Column 28, Line 57).

Please replace "-benzykuridine," with -- -benzyl-uridine; -- (Column 29, Line 22).

Please replace "-5-fluorouracil;" with -- -5-fluorouracil; 5'-O- -- (Column 29, Line 28).

Please replace "-5-isopropyluracil," with -- -5-isopropyluracil; -- (Column 29, Line 35).

Please replace "-(β-D-arabinafuranosyl)-" with -- -(β-D-arabinofuranosyl)- -- (Column 29, Line 37).

Please replace "hornodimers" with -- homodimers -- (Column 30, Line 26).

Please replace "L-uridine," with -- L-uridine, L-2',3'- -- (Column 30, Line 65).

CERTIFICATE OF CORRECTION (continued)
U.S. Pat. No. 12,194,043 B2

Please replace "carrier(s)," with -- carrier(s). -- (Column 31, Line 64).

Please replace "("patches")," with -- ("patches"). -- (Column 32, Line 53).

Please replace "amounts," with -- amounts. -- (Column 32, Line 58).

Please replace "available," with -- available. -- (Column 33, Line 20).

Please replace "Cobb" with -- cob -- (Column 38, Line 29).

Please replace "overdose," with -- overdose. -- (Column 39, Line 21).

Please replace "bleomycinipulmonary" with -- bleomycin/pulmonary -- (Column 39, Lines 39-40).

Please replace "bleomycinipulmonary" with -- bleomycin/pulmonary -- (Column 39, Line 47).

Please replace "matter," with -- matter. -- (Column 40, Line 12).

In the Claims

Please replace "derivativ" with -- derivative -- (Column 43, Line 24).

Please replace "fo" with -- for -- (Column 43, Line 30).